United States Patent
Yang et al.

(10) Patent No.: US 12,358,863 B2
(45) Date of Patent: Jul. 15, 2025

(54) NITROGEN-CONTAINING DERIVATIVE OF SUBSTITUTED PHENOL HYDROXY ACID ESTER, AND PREPARATION AND USE THEREOF

(71) Applicant: WEST CHINA HOSPITAL, SICHUAN UNIVERSITY, Sichuan (CN)

(72) Inventors: Jun Yang, Sichuan (CN); Jin Liu, Sichuan (CN); Weiyi Zhang, Sichuan (CN)

(73) Assignee: WEST CHINA HOSPITAL, SICHUAN UNIVERSITY, Sichuan (CN)

( * ) Notice: Subject to any disclaimer, the term of this patent is extended or adjusted under 35 U.S.C. 154(b) by 538 days.

(21) Appl. No.: 17/755,167

(22) PCT Filed: Oct. 16, 2020

(86) PCT No.: PCT/CN2020/121527
§ 371 (c)(1),
(2) Date: Apr. 22, 2022

(87) PCT Pub. No.: WO2021/078073
PCT Pub. Date: Apr. 29, 2021

(65) Prior Publication Data
US 2022/0388947 A1    Dec. 8, 2022

(30) Foreign Application Priority Data
Oct. 22, 2019    (CN) .......................... 201911009846.0

(51) Int. Cl.
| | | |
|---|---|---|
| *C07C 229/08* | (2006.01) | |
| *A61K 31/198* | (2006.01) | |
| *A61K 31/215* | (2006.01) | |
| *A61K 31/445* | (2006.01) | |
| *A61K 31/5375* | (2006.01) | |
| *A61P 23/00* | (2006.01) | |
| *A61P 25/00* | (2006.01) | |
| *C07C 53/18* | (2006.01) | |
| *C07C 69/01* | (2006.01) | |
| *C07C 229/12* | (2006.01) | |

(Continued)

(52) U.S. Cl.
CPC ............ *C07C 229/08* (2013.01); *A61P 23/00* (2018.01); *C07C 229/12* (2013.01); *C07C 237/06* (2013.01); *C07C 323/58* (2013.01); *C07D 205/04* (2013.01); *C07D 207/16* (2013.01); *C07D 211/60* (2013.01); *C07D 265/30* (2013.01); *C07D 295/15* (2013.01)

(58) Field of Classification Search
CPC ... C07C 229/08; C07C 229/12; C07C 237/06; C07C 323/58; C07C 2601/02; C07C 69/017; C07C 309/30; C07C 53/18; C07C 309/04; C07C 309/29; C07D 205/04; C07D 207/16; C07D 211/60; C07D 265/30; C07D 295/15; C07D 207/00; C07D 265/28; C07D 205/02; C07D 211/00; A61K 31/215; A61K 31/198; A61K 31/445; A61K 31/5375; A61P 23/00; A61P 25/00; C07B 2200/07
See application file for complete search history.

(56) References Cited

U.S. PATENT DOCUMENTS

2005/0004381 A1    1/2005  Gallop et al.

FOREIGN PATENT DOCUMENTS

| CN | 102381997 A | * | 3/2012 |
| CN | 102617380 A |   | 8/2012 |

(Continued)

OTHER PUBLICATIONS

Yang, J., W. Yin, J. Liu, Y. Wang, C. Zhou, Y. Kang, and W. Zhang, "Synthesis and characterization of novel quick-release propofol prodrug via lactonization", Bioorganic & Medicinal Chemistry Letters, vol. 23, Jan. 18, 2013, pp. 1813-1816. (Year: 2013).*

(Continued)

*Primary Examiner* — Joseph K McKane
*Assistant Examiner* — Sagar Patel
(74) *Attorney, Agent, or Firm* — NKL Law; Allen Xue

(57) ABSTRACT

A nitrogen-containing derivative of substituted phenol hydroxyl acid ester is represented by formula (I). A salt of the compound of formula (I) has good water solubility, and in vivo, can rapidly and completely release substituted phenols having a pharmacological effect, which can improve the water solubility of substituted phenols, rapidly exert the pharmacological effects of substituted phenols in vivo, and has good safety. The method for preparing the above-mentioned compound is provided. This compound can also be used in the preparation of drugs that produce anaesthesia and/or sedative and hypnotic effects on humans and animals.

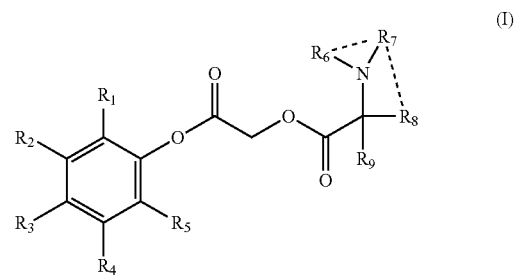

10 Claims, No Drawings

(51) Int. Cl.

| | |
|---|---|
| *C07C 237/06* | (2006.01) |
| *C07C 309/04* | (2006.01) |
| *C07C 309/29* | (2006.01) |
| *C07C 309/30* | (2006.01) |
| *C07C 323/58* | (2006.01) |
| *C07D 205/02* | (2006.01) |
| *C07D 205/04* | (2006.01) |
| *C07D 207/00* | (2006.01) |
| *C07D 207/16* | (2006.01) |
| *C07D 211/00* | (2006.01) |
| *C07D 211/60* | (2006.01) |
| *C07D 265/28* | (2006.01) |
| *C07D 265/30* | (2006.01) |
| *C07D 295/15* | (2006.01) |

(56) References Cited

FOREIGN PATENT DOCUMENTS

| WO | 2002013810 A1 | 2/2002 |
| WO | 2006017351 A1 | 2/2006 |
| WO | 2012142141 A1 | 10/2012 |

OTHER PUBLICATIONS

Liu, L., P. Hong, X. Song, C. Zhou, R. Ling, Y. Kang, Q. Qi and J. Yang, "Design, Synthesis, and Activity Study of Water-Soluble, Rapid-Release Propofol Prodrugs", J. Med. Chem. (2020), 63: pp. 7857-7866. (Year: 2020).*

English translation of CN 102381997 A, https://patents.google.com/patent/CN102381997A/en?oq=CN102381997A, Retrieved on Sep. 26, 2024. (Year: 2024).*

Yang, Jun et al.; "Synthesis and characterization of novel quick-release propofol prodrug via lactonization"; Bioorganic & Medicinal Chemistry Letters; vol. 23, Jan. 18, 2013; pp. 1813-1816.

Altomare, Cosimo et al.; "Highly water-soluble derivatives of the anesthetic agent propofol: in vitro and in vivo evaluation of cyclic amino acid esters"; European Journal of Pharmaceutical Sciences; vol. 20; Dec. 31, 2003; pp. 17-26.

Macario, Alex et al.; "Which Clinical Anesthesia Outcomes Are Both Common and Important to Avoid? The Perspective of a Panel of Expert Anesthesiologists"; Anesth Analg; May 1999; vol. 88; pp. 1085-1091.

Bennett, Siiri N. et al.;"Postoperative Infections Traced To Contamination of an Intravenous Anesthetic, Propofol"; the New England Journal of Medicine; Jul. 20, 1995; vol. 333; No. 3; pp. 147-154.

Kam, P.C.A. et al.; "Review Article Propofol infusion syndrome"; Anesthesia; 2007; vol. 62, No. 7; pp. 690-701.

Wolf, Andrew et al.; "Impaired fatty acid oxidation in propofol infusion syndrome"; The Lancet; Feb. 24, 2001; vol. 357(9256); pp. 606-607.

Fechner, J. et al.; "Comparative Pharmacokinetics and Pharmacodynamics of the New Propofol Prodrug GPI 15715 and Propofol Emulsion"; Anesthesiology; 2004; vol. 101, No. 3; pp. 626-639.

Tao Deng et al.; "Monodisperse oligoethylene glycols modified Propofol prodrugs"; Bioorganic&Medicinal Chemistry Letters; Dec. 2018; vol. 28; pp. 3502-3505.

Weiyi Zhang et al.; "An improved water-soluble prodrug of propofol with high molecular utilization and rapid onset of action"; European Journal of Pharmaceutical Sciences; Jan. 2019; vol. 127; No. 15; pp. 9-13.

* cited by examiner

NITROGEN-CONTAINING DERIVATIVE OF SUBSTITUTED PHENOL HYDROXY ACID ESTER, AND PREPARATION AND USE THEREOF

TECHNICAL FIELD

The present invention relates to the chemical structure, preparation method and use of water-soluble prodrug molecules for a kind of substituted phenols. Such molecules can quickly break down in vivo and release active substituted phenols, with fast onset of action. The availability of substituted phenols was high, and their intake amount was small.

BACKGROUND TECHNOLOGY

The present invention belongs to the research field of prodrugs among chemical drugs. Prodrugs are a class of non-active drugs that enter the body, release the active prototype drug under the action of enzymes, and thus exerts the curative effect. Compared with the prototype drug, the prodrug molecule has different physical and chemical properties due to obvious changes in the chemical structure, such as changes in water solubility, fat solubility, stability, and so on. Using prodrug design, the shortcomings of the prototype drug can be improved, such as increasing its efficacy, tolerance, industrial applicability, etc. Propofol is a first-line intravenous anesthetic, which is hardly soluble in water. Currently, the clinical preparation is emulsion. Emulsions are costly to prepare, susceptible to bacterial contamination, have a high incidence of injection pain, and can lead to lipid metabolism disorders in a subject when used for a long time (Macario, A., Weinger, M., Truong, P., Lee, M., 1999. Anesth. Analg. 88, 1085-1091; Bennett, S. N., McNeil, M. M., Bland, L. A., Arduino, M. J., Villarino, M. E., Perrotta, D. M., et al., 1995. N. Engl. J. Med. 333 (3), 147-154; Kam, P. C., Cardone, D., 2007. Anesthesia 62 (7), 690-701; Wolf, A., Weir, P., Segar, P., Stone, J., Shield, J., 2001. Lancet 357 (9256), 606-607)). Therefore, the water-soluble prodrugs of propofol have always been the focus of drug research and development. Prodrug molecules with improved water solubility can be obtained by covalently linking propofol to water-soluble molecules, such as propofol-amino acid conjugates (Gallop, Mark A., Xu, Feng, Cundy, Kenneth C., Sasikumar, Vivek, Woiwode, Thomas W., 2005. US20050004381), propofol-glycosyl conjugates (Brian, Shull, John, Baldwin, Ramesh, Gopalaswamy, Zishan, Haroon, 2012. WO2012142141), propofol-phosphate conjugates (Fechner, J., Ihmsen, H., Hatterscheid, D., Jeleazcov, C., Schiessl, C., Vornov, J. J., Schwilden, H., Schuttler, J., 2004. Anesthesiology 101 (3), 626-639), propofol-organic polyacid conjugates (Hendler, Sheldon S., 2002. WO2002013810), propofol-oligo-polyethylene glycol conjugates (Tao Deng, Xianglan Mao, Yu Li, Shaowei Bo, Zhigang Yang, Zhong-Xing Jiang, 2018. Bioorganic & Medicinal Chemistry Letters 28, 3502-3505) and the like. Numerous water-soluble derivatives of propofol have been synthesized, and attempts have been made to develop them into pharmaceuticals. In 2008, fospropofol, the first water-soluble prodrug of propofol, was marketed in the United States, but was subsequently withdrawn for unknown reasons. As of 2019, no new water-soluble prodrug of propofol was marketed.

The greatest clinical advantage of propofol is characterized by quickly effect and rapid recovery after drug withdrawal. Clinicians hope that the water-soluble prodrugs of propofol can also retain this advantage. If the water-soluble prodrug of propofol is unable to release propofol rapidly in the body, the prodrug will lose the advantage of quick acting; further, if the prodrug releases the prototype drug slowly, the dose of the prodrug will have to be increased in order to maintain the effective plasma concentration of the prototype drug, and thus the remaining prodrug in the body will continue to release propofol, resulting in delayed recovery. The onset time of fospropofol and its duration of anesthetic maintenance were significantly longer than those of propofol because of its slow release of propofol in vivo. Therefore, some scholars have proposed that accelerating the release rate of propofol prodrugs in the body and improving the molecular utilization rate of prodrugs are the key to the development of such prodrugs, which can not only retain the clinical advantages of propofol, but also reduce the intake amount of prodrugs, improve the quality of awakening and increase the safety (Weiyi Zhang, Jun Yang, Jing Fan, Bin Wang, Yi Kang, Jin Liu, Wensheng Zhang, Tao Zhu. European Journal of Pharmaceutical Sciences, 2019, 9-13).

The above conditions require that the water-soluble prodrug of propofol has enough stability in vitro to be able to be produced, transported, and stored; and the prodrug must release propofol as soon as possible after entering the body, in order to take effect quickly and ensure rapid recovery of the patient after withdrawal. Such contradictory requirements make the development of water-soluble propofol prodrugs extremely difficult, and no propofol prodrugs have yet been found to be able to meet these requirements at the same time under the conditions of ensuring safety, which limits the development of such drugs.

In view of the above problems, the present invention provides a water-soluble prodrug of substituted phenols including propofol. These molecules are stable in vitro and have good water solubility; once entering the body, the substituted phenol conjugated in the molecule can be released rapidly and completely by the action of plasma. Intravenous administration of these molecules can produce anesthetic effect immediately after injection; due to their rapid release, the time required for these molecules to produce anesthetic effect is equivalent to that required for the direct use of propofol, and the molar amount of prodrug at the effective dose is close to that of propofol, thus causing no delay in awakening due to slow release of the prodrug. The animals in the experiment had fast awakening speed and good awakening quality, and there was no difference compared with the control animals of propofol. This class of molecules provided in the present invention completely solves the problem of slow release of the propofol prodrug, minimizes the intake of the prototype drug, has good safety, and possesses an excellent application prospect. In conclusion, the compounds of formula (I) and the pharmaceutically acceptable salts thereof can be used for the preparation of central inhibitory drugs that produce sedative, hypnotic and/or anesthetic effects on animals or humans.

Content of the Invention

The present invention provides a kind of water-soluble precursor molecules of substituted phenols including propofol, and a preparation method and use thereof. At the effective dose, these molecules can rapidly break down and release substituted phenols in the body of animals, and thus produce a rapid effect, without accumulation effect caused by slow release of prototype drug. On the condition of improving the water solubility of substituted phenols, the advantages of rapid onset and recovery of substituted phenols are retained.

The nitrogen-containing derivative of substituted phenol hydroxy acid ester according to the present invention contains has a structure of formula (I):

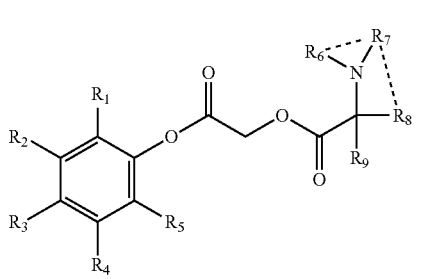

wherein, $R_1$-$R_5$ are each independently selected from the group consisting of H, $C_{1-6}$ linear or branched or cyclic hydrocarbyl, halogen, $C_{1-4}$ alkoxy, cyano, nitro, ester group, etc.; $R_6$-$R_9$ are each independently selected from the group consisting of H, and $C_{1-8}$ linear or branched or cyclic hydrocarbyl; when $R_7$ and $R_8$ are covalently linked, $R_7$ and $R_8$ can also be $C_{1-3}$ alkylenes; H in the skeleton of $R_{1-9}$ can be substituted with halogen, hydroxyl, sulfhydryl, carbamoyl, guanidyl, carboxyl, 4-imidazolyl, phenyl, hydroxyphenyl, β-indolyl, etc.; $R_{1-9}$ skeleton can contain O, S, N and other heteroatoms.

The salt of the compound of formula (I) includes but is not limited to the group consisting of acetate, adipate, alginate, 4-aminosalicylate, ascorbate, aspartate, glutamate, pyroglutamate, benzenesulfonate, benzoate, butyrate, camphorate, camphorsulfonate, carbonate, cinnamate, citrate, cyclohexaminesulfonate, cyclopentanepropionate, decanoate, 2,2-dichloroacetate, digluconate, dodecylsulphate, ethane-1,2-disulfonate, ethanesulfonate, formate, fumarate, mucate, gentisate, glucoheptanate, gluconate, glucuronate, glycerophosphate, hydroxyacetate, semisulfate, heptanoate, caproate, hippurate, hydrochloride, hydrobromide, hydroiodate, 2-hydroxyethanesulfonate, isobutyrate, lactate, lactobionate, laurate, malate, maleate, malonate, mandelate, methanesulfonate, naphthalene-1,5-disulfonate, 2-naphthalenesulfonate, nicotinate, nitrate, octanoate, oleate, orotate, oxalate, 2-oxoglutarate, palmitate, pamoate, pectinate, persulfate, 3-phenylpropionate, phosphate, picrate, pivalate, propionate, salicylate, sebacate, bisebacate, stearate, succinate, sulfate, tannate, tartrate, bitartrate, thiocyanate, toluenesulfonate or undecylate, hydrogen sulfate, sodium, ammonium.

Further, for the compound of formula (I), the scope of each substituent is preferably that $R_1$-$R_5$ are each independently selected from the group consisting of H, and $C_{1-6}$ linear or branched or cyclic hydrocarbyl; $R_6$-$R_9$ are each independently selected from the group consisting of H, and $C_{1-8}$ linear or branched or cyclic hydrocarbyl; H in the skeleton of $R_{1-9}$ can be substituted with hydroxyl, sulfhydryl, carbamoyl, guanidyl, carboxyl, 4-imidazolyl, phenyl, hydroxyphenyl, β-indolyl, etc.; $R_{1-9}$ skeleton can contain O, S, N and other heteroatoms;

alternatively, for the compound of formula (I), the scope of each substituent is preferably that $R_1$-$R_5$ are each independently selected from the group consisting of H, and $C_{1-6}$ linear or branched or cyclic hydrocarbyl; $R_6$ and $R_7$ are covalently linked, and $R_6$ and $R_7$ are $C_{1-3}$ alkylenes; $R_8$ and $R_9$ are each independently selected from the group consisting of H, and $C_{1-8}$ linear or branched or cyclic hydrocarbyl;

alternatively, for the compound of formula (I), the scope of each substituent is preferably that $R_1$-$R_5$ are each independently selected from the group consisting of H, and $C_{1-6}$ linear or branched or cyclic hydrocarbyl; $R_7$ and $R_8$ are covalently linked, and $R_7$ and $R_8$ are $C_{1-3}$ alkylenes; $R_6$ and $R_9$ are each independently selected from the group consisting of H, and $C_{1-8}$ linear or branched or cyclic hydrocarbyl.

Further, for the compound of formula (I), the scope of each substituent is preferably that $R_1$ and $R_5$ are isopropyl; $R_2$-$R_4$ are H; $R_6$-$R_9$ are each independently selected from the group consisting of H, and $C_{1-8}$ linear or branched or cyclic hydrocarbyl; when $R_6$ and $R_7$ are covalently linked, $R_6$ and $R_7$ can also be $C_{1-3}$ alkylenes; when $R_7$ and $R_8$ are covalently linked, $R_7$ and $R_8$ can also be $C_{1-3}$ alkylenes; H in the skeleton of $R_{1-9}$ can be substituted with halogen, hydroxyl, sulfhydryl, carbamoyl, guanidyl, carboxyl, 4-imidazolyl, phenyl, hydroxyphenyl, β-indolyl, etc., and $R_{1-9}$ skeleton can contain O, S, N and other heteroatoms. The preferred specific molecules for these compounds are selected from the group consisting of following structures:

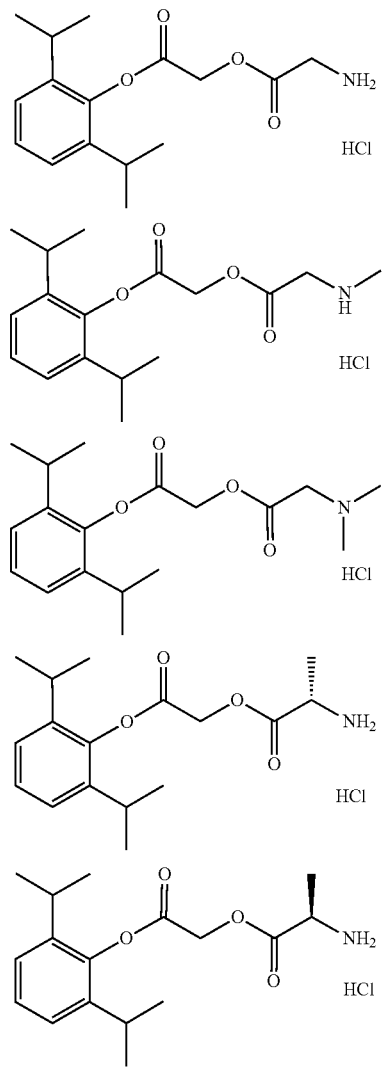

Alternatively, further, for the compound of formula (I), the scope of each substituent is preferably that $R_1$ is isopropyl; $R_5$ is

[structures shown]

$R_2$-$R_4$ are H; $R_6$-$R_9$ are each independently selected from the group consisting of H, and $C_{1-8}$ linear or branched or cyclic hydrocarbyl; when $R_6$ and $R_7$ are covalently linked, $R_6$ and $R_7$ can also be $C_{1-3}$ alkylenes; when $R_7$ and $R_8$ are covalently linked, $R_7$ and $R_8$ can also be $C_{1-3}$ alkylenes; H in the skeleton of $R_{1-9}$ can be substituted with halogen, hydroxyl, sulfhydryl, carbamoyl, guanidyl, carboxyl, 4-imidazolyl, phenyl, hydroxyphenyl, β-indolyl, etc., and $R_{1-9}$ skeleton can contain O, S, N and other heteroatoms. The preferred specific molecules for these compounds are selected from the group consisting of following structures:

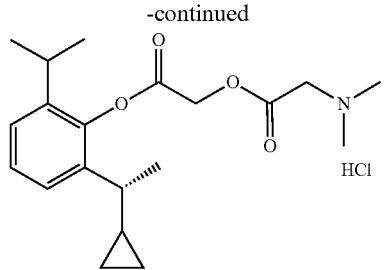
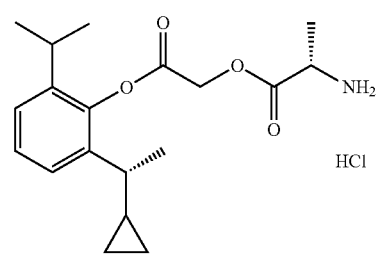
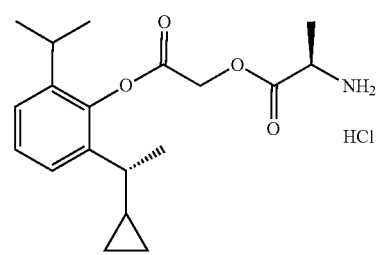
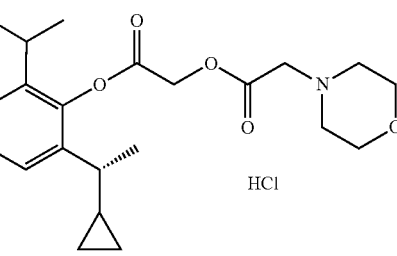
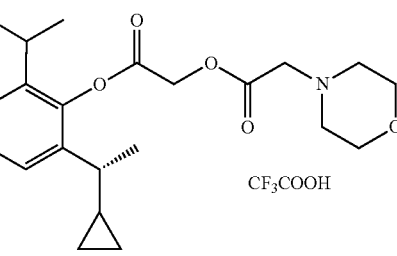
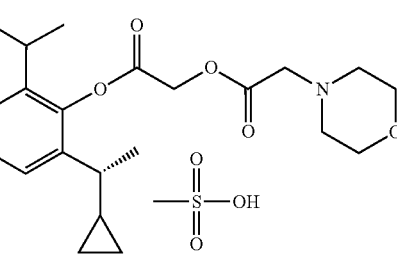
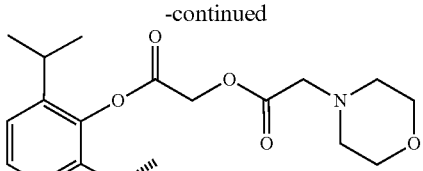
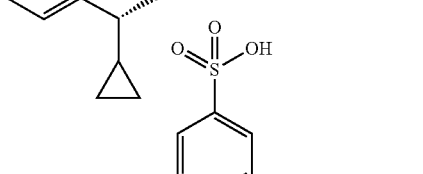
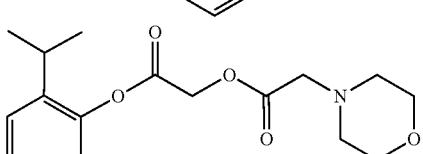
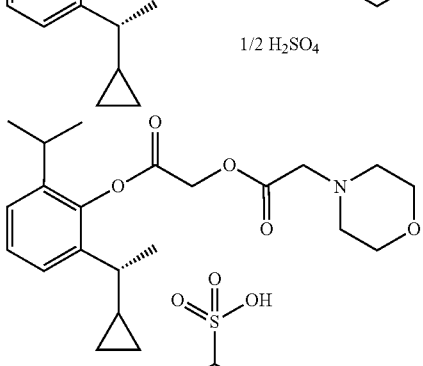
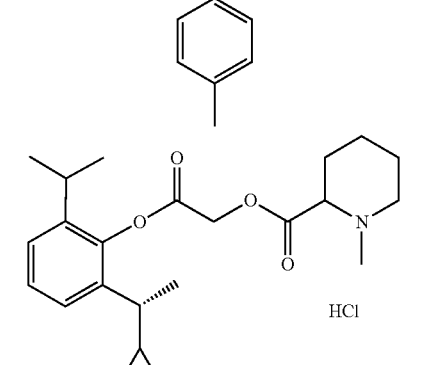
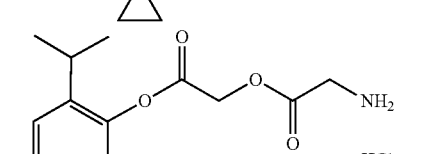
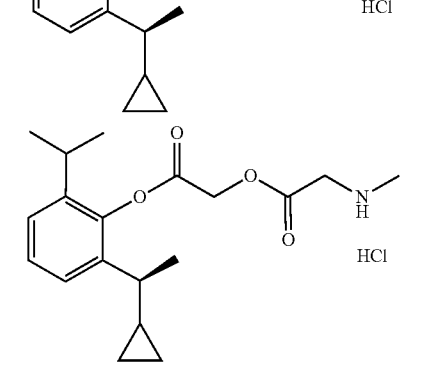

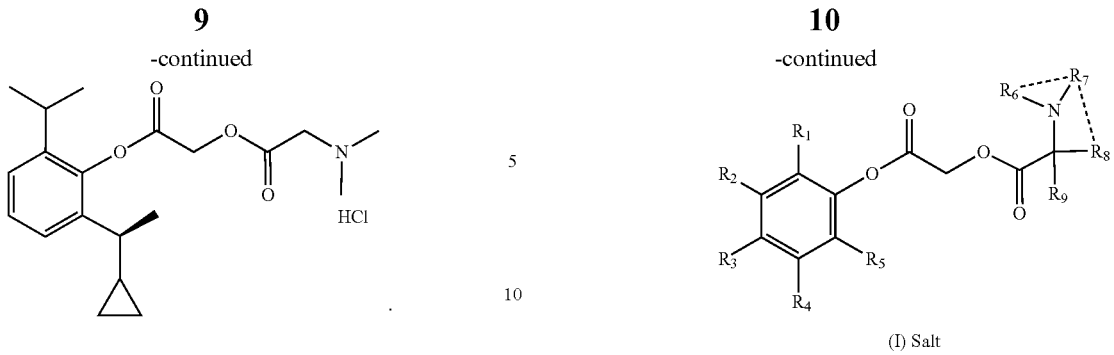

According to the common knowledge in this field, the formulation prepared from a compound of formula (I), and a stereoisomer, an isotopically substituted compound, a pharmaceutically acceptable salt, a solvate, a pharmaceutical composition thereof, and pharmaceutically acceptable excipients/carriers/adjuvents, etc., may be used in the preparation of a medicament that has central sedative actions and/or anesthetic effects on humans or animals.

The compound according to the present invention can be prepared according to the following general procedures:

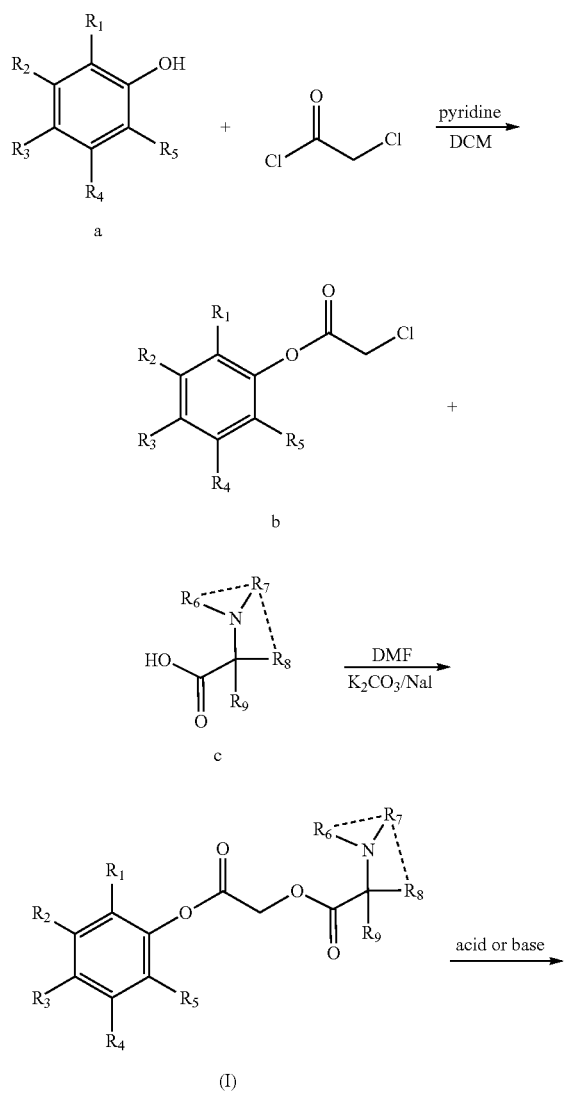

A chloroacetate compound (b) of substituted phenols is firstly prepared by the esterification of chloroacetyl chloride and substituted phenols (a), and then a free base of the target compound (I) is synthesized by a nucleophilic substitution reaction of (b) with a nitrogen-containing carboxylic acid compound (c) under basic conditions, and the resultant free base can form different salts with different acids. If the molecule of formula (I) contains a carboxyl group, (I) can also react with alkaline reagents such as sodium carbonate to obtain the salt of (I). In the above synthetic method, chloroacetyl chloride can also be replaced by bromoacetyl bromide with higher activity.

In the above reaction procedures, if N atom in the N-containing carboxylic acid compound (c) is a primary or secondary amine, the amino group can be firstly protected by a protective group (such as BOC protection), and then the intermediate containing the protective group can be obtained by reacting with (b). Subsequently, the target compound (I) can be obtained by removing the amino protecting group.

Unless a contrary statement, the terms used in the specification and claims have the following meanings.

The carbon, hydrogen, oxygen, sulfur, nitrogen or halogens contained in the groups and compounds of the present invention all include their isotopes, and are optionally further substituted with one or more of their corresponding isotopes (i. e., isotope substitutions), wherein the isotopes of carbon include $^{12}C$, $^{13}C$ and $^{14}C$; the isotopes of hydrogen include protium (H), deuterium (D, also known as heavy hydrogen) and tritium (T, also known as superheavy hydrogen); the isotopes of oxygen include $^{16}O$, $^{17}O$, and $^{18}O$; the isotopes of sulfur include $^{32}S$, $^{33}S$, $^{34}S$, and $^{36}S$; the isotopes of nitrogen include $^{14}N$ and $^{15}N$; the isotope of fluorine includes $^{19}F$; the isotopes of chlorine include $^{35}C_1$ and $^{37}Cl$; and the isotopes of bromine include $^{79}Br$ and $^{81}Br$.

"Hydrocarbyl" means a linear or branched or cyclic monovalent substituent containing only carbon and hydrogen atoms, whose main chain comprises 1 to 10 carbon atoms, preferably 1 to 8 carbon atoms, and further preferably 1 to 6 carbon atoms. The hydrocarbyl may be a linear or branched or cyclic alkyl/alkenyl/alkynyl. The hydrocarbyl can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)a$-(C=O)—$SR_{10}$, —$(CH_2)a$-(C=O)—O—$R_{10}$, —$(CH_2)a$-(C=O)—$NR_{10}R_{10a}$, —$(CH_2)a$-S(C=O)$_b$—$R_{10}$, —O—(=O)—O—$R_{10}$, or —$NR_{10}R_{10a}$, in which $R_{10}$ and $R_{10a}$ are each independently selected from the group consisting of H, hydroxyl, amino, carboxyl, $C_{1-8}$ alkyl, $C_{1-8}$ alkoxy, $C_{2-8}$ alkenyl, $C_{2-8}$ alkynyl, 3 to 10-membered carbyclyl, 4 to 10-membered heterocyclyl, 3 to 10-membered carbyclyloxy, or 4 to 10-membered heterocyclyloxy, and a is selected from the group consisting of 0, 1, 2, 3, 4, and 5, while b is selected from the group consisting of 0, 1 and 2. The alkyl, a, b, $R_{10}$ and $R_{10a}$, as used herein, are defined as described above.

"Alkyl" means a linear and branched monovalent saturated hydrocarbyl, whose main chain comprises 1 to 10 carbons, preferably 1 to 8 carbons, further preferably 1 to 6 carbons, more preferably 1 to 4 carbon atoms, and most preferably 1 to 2 carbon atoms. Examples of alkyl groups include but are not limited to methyl, ethyl, n-propyl, isopropyl, n-butyl, isobutyl, sec-butyl, t-butyl, n-amyl, 2-amyl, 3-amyl, 2-methyl-2-butyl, 3-methyl-2-butyl, n-hexyl, n-heptyl, n-octyl, n-nonyl, and n-decyl. The alkyl can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$, in which $R_{10}$ and $R_{10a}$ are each independently selected from the group consisting of H, hydroxyl, amino, carboxyl, $C_{1-8}$ alkyl, $C_{1-8}$ alkoxy, $C_{2-8}$ alkenyl, $C_{2-8}$ alkynyl, 3 to 10-membered carbyclyl, 4 to 10-membered heterocyclyl, 3 to 10-membered carbyclyloxy, or 4 to 10-membered heterocyclyloxy, and a is selected from the group consisting of 0, 1, 2, 3, 4, and 5, while b is selected from the group consisting of 0, 1 and 2. The alkyl, a, b, $R_{10}$ and $R_{10a}$, as used herein, are defined as described above.

"Hydrocarbylene" means both straight and branched divalent saturated or unsaturated hydrocarbons, where the saturated hydrocarbylene is also called an alkylene, which is expressed as —$(CH_2)$k- (k is an integer of from 1 to 10). The examples of alkylene include but are not limited to methylene, ethylene, propylene, and butylene; said alkylene can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$. When the number of substituents in the alkylene group is greater than or equal to 2, the substituents can be fused together to form a cyclic structure. The alkylene as used herein is defined as described above.

"Alkoxy" means the monovalent group of O-alkyl, where the alkyl is as defined herein. The examples of alkoxy include, but are not limited to methoxy, ethoxy, 1-propoxy, 2-propoxy, 1-butoxy, 2-methyl-1-propoxy, 2-butoxy, 2-methyl-2-propoxy, 1-pentoxy, 2-pentoxy, 3-pentoxy, 2-methyl-2-butoxy, 3-methyl-2-butoxy, 3-methyl-1-butoxy and 2-methyl-1-butoxy, etc. The alkoxy, as used herein, are defined as described above.

"Alkenyl" refers to a linear and branched monovalent unsaturated hydrocarbyl having at least one, usually 1, 2 or 3 C=C double bonds, whose main chain comprises 2 to 10 carbons, further preferably 2 to 6 carbons, and more preferably 2 to 4 carbons. The examples of alkenyl include but are not limited to vinyl, propenyl, 1-propenyl, 2-propenyl, 1-butenyl, 2-butenyl, 3-butenyl, 1-pentenyl, 2-pentenyl, 3-pentenyl, 4-pentenyl, 1-methyl-1-butenyl, 2-methyl-1-butenyl, 2-methyl-3-butenyl, 1-hexenyl, 2-hexenyl, 3-hexenyl, 4-hexenyl, 5-hexenyl, 1-methyl-1-pentenyl, 2-methyl-1-pentenyl, 1-heptenyl, 2-heptenyl, 3-heptenyl, 4-heptenyl, 1-octenyl, 3-octenyl, 1-nonenyl, 3-nonenyl, 1-decenyl, 4-decenyl, 1,3-butadiene, 1,3-pentadiene, 1,4-pentadiene and 1,4-hexadiene, etc. Said alkenyl can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$. The alkenyl, as used herein, is defined as described above.

"Alkynyl" refers to a linear and branched monovalent unsaturated hydrocarbyl having at least one, usually 1, 2 or 3 CC double bonds, whose main chain includes but is not limited to ethynyl, 1-propynyl, 2-propynyl, butynyl, 2-butynyl, 3-butynyl, 1-methyl-2-propynyl, 3-pentynyl, 4-pentynyl, 1-methyl-2-butynyl, 2-hexynyl, 2-heptynyl, 3-heptynyl, 4-heptynyl, 3-octynyl, 3-nonynyl and 4-nonynyl, etc. Said alkynyl can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$. The alkynyl, as used herein, is defined as described above.

"Cycloalkyl" means a monovalent saturated carbocyclic hydrocarbyl, generally having 3 to 10 carbons, and non-limiting examples include cyclopropyl, cyclobutyl, cyclopentyl, cyclohexyl, or cycloheptyl, etc. Said cycloalkyl can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$. The cycloalkyl, as used herein, is defined as described above.

"Carbocyclic ring" means a saturated or unsaturated, aromatic or non-aromatic ring. The aromatic or non-aromatic ring may be a 3 to 10-membered monocyclic ring, 4 to 12-membered bicyclic ring, or 10 to 15-membered tricyclic ring, and the carbocyclic group may be connected with a bridged ring or spiro ring. Non-limiting examples include cyclopropyl, cyclobutyl, cyclopentyl, 1-cyclopent-1-enyl, 1-cyclopent-2-enyl, 1-cyclopent-3-enyl, cyclohexyl, 1-cyclohex-2-enyl, 1-cyclohex-3-enyl, cyclohexenyl, cyclohexadienyl, cycloheptyl, cyclooctyl, cyclononyl, cyclodecyl, cyclododecyl, phenyl, or naphthyl. Said carbocyclic ring can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)$a-(C=O)—$SR_{10}$, —$(CH_2)$a-(C=O)—O—$R_{10}$, —$(CH_2)$a-(C=O)—$NR_{10}R_{10a}$, —$(CH_2)$a-S(C=O)$_b$—$R_{10}$, —O—(=O)—O—$R_{10}$ or —$NR_{10}R_{10a}$. The carbocyclic ring, as used herein, is defined as described above.

"heterocycle" means a saturated or unsaturated, aromatic or non-aromatic ring. The aromatic or non-aromatic ring may be a 3 to 10-membered monocyclic ring, 4 to 10-membered bicyclic ring, or 10 to 15-membered tricyclic ring, and contain 1 to 4 heteroatoms selected from the group consisting of N, O, and S, and 3 to 8-membered heterocyclic groups are preferable, in which optionally substituted N and S can be oxidized to various oxidation states. The heterocyclic group can be attached to a heteroatom or a carbon, and linked with a bridged ring or a spiro ring. Non-limiting examples include oxiranyl, epoxypropyl, aziridinyl, oxetanyl, azetidinyl, thietanyl, 1,3-dioxolanyl, 1,4-dioxolanyl, 1,3-dioxanyl, azepanyl, oxacycloheptyl, thiacycloheptyl, oxazepinyl, diazepinyl, thiazepinyl, pyridyl, piperidyl, homopiperidinyl, furyl, thienyl, pyranyl, N-alkylpyrrolyl, pyrimidinyl, pyrazinyl, pyridazinyl, piperazinyl, homopiperazinyl, imidazolyl, piperidinyl, morpholinyl, thiomorpholinyl, thioxanyl, 1,3-dithiophenyl, dihydrofuryl, dihydropyranyl, dithiolanyl, tetrahydrofuryl, tetrahydrothiophenyl, tetrahydropyranyl, tetrahydrothiopyranyl, tetrahydropyrrolyl, tetrahydroimidazolyl, tetrahydrothiazolyl, benzimidazolyl, benzopyridyl, pyrrolopyrrolyl, benzodihydrofuranyl, 2-pyrrolinyl, 3-pyrrolinyl, dihydroindolyl, dihydrothiophenyl, pyrazolidinyl, imidazolinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolylquinalizinyl, N-pyridylurea, 1,1-dioxothiomorpholinyl, azabicyclo[3.2.1]octane, azabicyclo[5.2.0]nonane, oxatricyclo[5.3.1.1]dodecyl, azaadamantanyl, and oxaspiro[3.3]heptane. Said heterocyclic group can optionally be further substituted with 0, 1, 2, 3, 4 or 5 substituents selected from the group consisting of F, Cl, Br, I, =O, hydroxyl, —$SR_{10}$, nitro, cyano, $C_{1-6}$ alkyl, $C_{1-6}$ hydroxyalkyl, $C_{1-6}$ alkoxy, $C_{2-6}$ alkenyl, $C_{2-6}$ alkynyl, $C_{3-8}$ carbocyclyl, 3 to 8-membered heterocyclyl, —$(CH_2)a$-(C=O)—$SR_{10}$, —$(CH_2)a$-(C=O)—O—$R_{10}$, —$(CH_2)a$-(C=O)—$NR_{10}R_{10a}$, —$(CH_2)a$-S(C=O)$_b$—$R_{10}$, —O—(=O)—O—$R_{10}$ or —$NR_{10}R_{10a}$. The heterocycle, as used herein, is defined as described above.

"Optionally" means that a subsequent description of an event or environment may, but does not have to, occur, and that description includes situations where the event or environment occurs or does not occur.

"A pharmaceutical composition" means a mixture of one or more of the compounds described herein or a physiologically/pharmaceutically acceptable salt thereof, and other components, wherein the other components comprise physiologically/pharmaceutically acceptable carriers and excipients.

"Carrier" means a vehicle or diluent that does not produce a significant stimulus to the organism and does not eliminate the biological activity and properties of the given compound.

"Excipient" refers to an inert substance added to the pharmaceutical composition to further rely on the administration of a compound. Examples of excipients include, but are not limited to, calcium carbonate, calcium phosphate, various sugars and different types of starch, cellulose derivatives (including microcrystalline cellulose), gelatin, vegetable oils, polyethylene glycol, diluents, granulating agents, lubricants, binders, disintegrants, and the like.

"Stereoisomers" refer to isomers resulting from different spatial arrangements of atoms in a molecule, including cis-trans isomers, enantiomers, and conformational isomers.

"Effective dose" means the amount of a compound that causes a physiological or medical response in a tissue, system, or subject, which is found out, including the amount of a compound that, when administered to a subject, is sufficient to prevent or alleviate to some extent one or more symptoms of the diseases or conditions treated.

"Solvate" refers to a compound of the present invention or a salt thereof, which comprises a stoichiometric or non-stoichiometric solvent by binding in a non-covalent intermolecular force. When the solvent is water, it is a hydrate.

By the following specific examples of said embodiments, the above content of the present invention is further illustrated. But it should not be construed that the scope of the above subject matter of the present invention is limited to the following examples. Without department from the above basic technical spirits of the present invention, other various alternations or changes can further be made, according to the common technical knowledge and the conventional means in the field, that should be all within the scope of the present invention.

EXAMPLES

Example 1

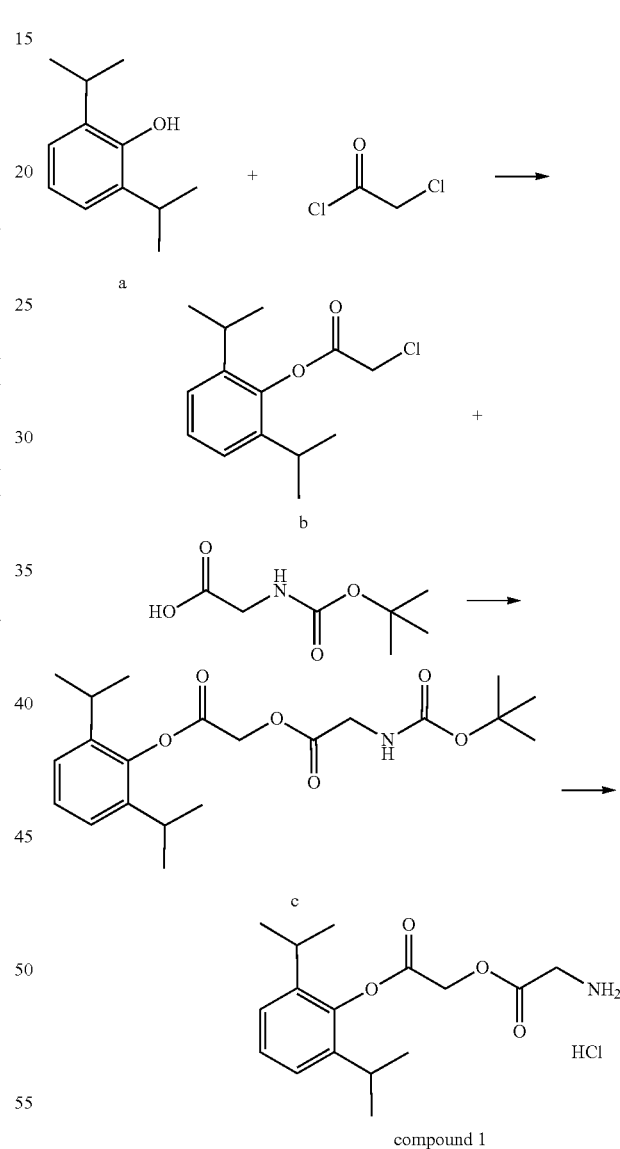

Propofol (178 mg, 1 mmoL) and chloroacetyl chloride (124 mg, 1.1 mmoL) were dissolved in 10 mL of dichloromethane, to which was added pyridine (237 mg, 3 mmoL) in an ice bath, and then the reaction solution was warmed to room temperature and stirred for 2 h. The solvent was evaporated to dry, and the residue was subjected to silica gel column chromatography (cyclohexane/ethyl acetate=20/1) to obtain the intermediate b as colorless oils (180 mg), with a yield of 70.6%.

Intermediate b (180 mg, 71 mmoL) and BOC-glycine (140 mg, 80 mmoL) were mixed in 10 mL of DMF, to which was added anhydrous potassium carbonate (290 mg, 210 mmoL), and then the reaction solution was stirred at room temperature for 8 h and filtered. The filtrate was poured into 100 mL of water, and then extracted with 50 mL of ethyl acetate. The organic layer was separated out, dried overnight with anhydrous sodium sulfate, and filtered the next day. The filtrate was evaporated to dry under reduced pressure, and the residue was subjected to column chromatography (cyclohexane/ethyl acetate=5/1) to yield 183 mg of white solid powder, i.e. intermediate c, with a yield of 66%. 183 mg of intermediate c was dissolved in 10 mL of ethyl acetate, and then excess dry HCl gas was purged. The reaction solution was stirred for 1 h at room temperature, and the solvent was evaporated to dry under reduced pressure, to obtain the crude product. The crude product was rinsed with cyclohexane for 3 times and subjected to suction filtration. The filter cake was dried at 65° C. to obtain 115 mg of target compound 1 as a white solid, with a yield of 75%.

$^1$H NMR (400 MHz, DMSO-d$_6$): δ 8.52 (s, 3H), 7.23-7.31 (m, 3H), 5.29 (s, 2H), 4.00 (s, 2H), 2.94 (hept, J=6.9 Hz, 2H), 1.13 (d, J=6.8 Hz, 12H).

Example 2

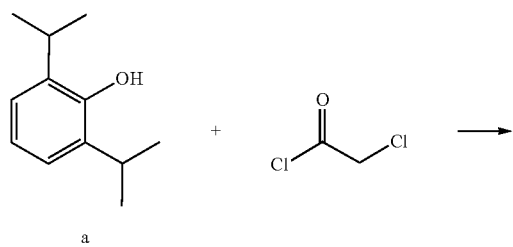

a

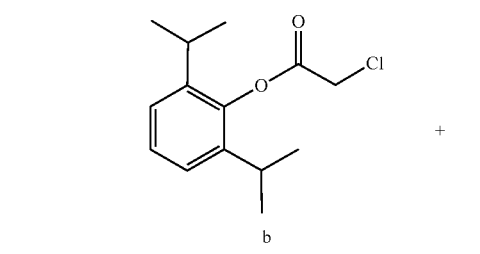

b

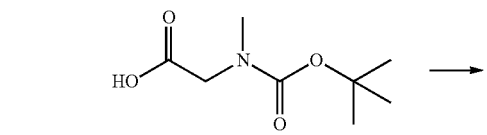

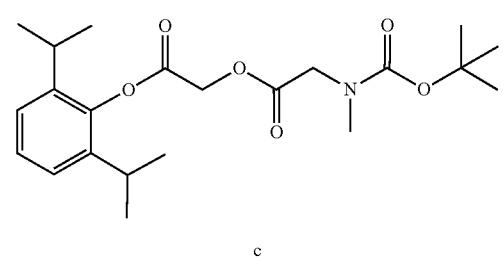

c

-continued

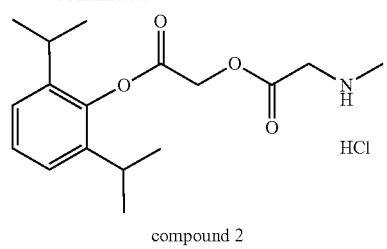

compound 2

The intermediate b was prepared as described in Example 1. Intermediate b (180 mg, 71 mmoL) and BOC-sarcosine (151 mg, 80 mmoL) were mixed in 10 mL of DMF, to which was added anhydrous potassium carbonate (290 mg, 210 mmoL), and then the reaction solution was stirred at room temperature for 8 h and filtered. The filtrate was poured into 100 mL of water, and then extracted with 50 mL of ethyl acetate. The organic layer was separated out, dried overnight with anhydrous sodium sulfate, and filtered the next day. The filtrate was evaporated to dry under reduced pressure, and the residue was subjected to column chromatography (cyclohexane/ethyl acetate=5/1) to yield 186 mg of white solid powder, i.e. intermediate c, with a yield of 64.5%. 186 mg of intermediate c was dissolved in 10 mL of ethyl acetate, and then excess dry HCl gas was purged. The reaction solution was stirred for 1 h at room temperature, and the solvent was evaporated to dry under reduced pressure, to obtain the crude product. The crude product was rinsed with cyclohexane for 3 times and subjected to suction filtration. The filter cake was dried at 65° C. to obtain 113 mg of target compound 2 as a white solid, with a yield of 72%.

$^1$H NMR (400 MHz, DMSO-d$_6$): δ 9.46 (s, 2H), 7.23-7.31 (m, 3H), 5.31 (s, 2H), 4.17 (s, 2H), 2.94 (hept, J=6.8 Hz, 2H), 2.59 (s, 3H), 1.13 (d, J=6.8 Hz, 12H).

Example 3

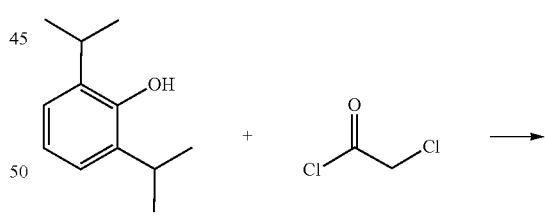

a

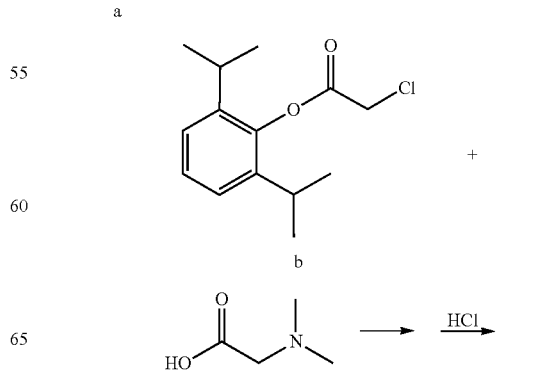

b

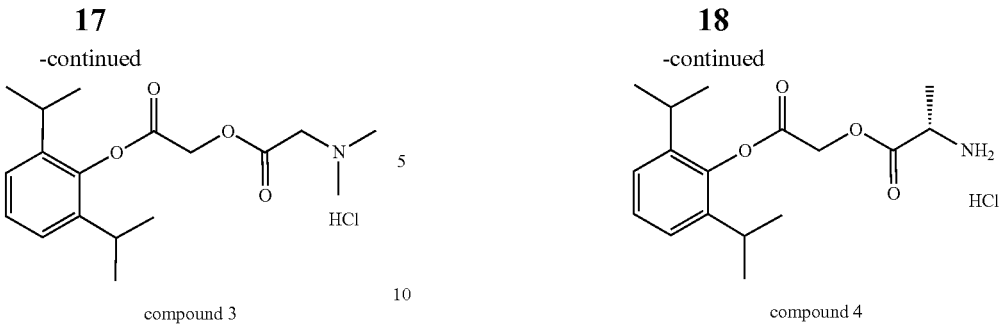

compound 3 compound 4

The intermediate b was prepared as described in Example 1. Intermediate b (180 mg, 71 mmoL) and N,N-dimethylglycine (82.4 mg, 80 mmoL) were mixed in 10 mL of DMF, to which was added anhydrous potassium carbonate (290 mg, 210 mmoL), and then the reaction solution was stirred at room temperature for 8 h and filtered. The filtrate was poured into 100 mL of water, and then extracted with 50 mL of ethyl acetate. The organic layer was separated out, dried overnight with anhydrous sodium sulfate, and filtered the next day. The filtrate was evaporated to dry under reduced pressure, and the residue was subjected to column chromatography (cyclohexane/ethyl acetate=30/1) to yield 123 mg of compound 3 as free base. 123 mg of compound 3 as free base was dissolved in 10 mL of ethyl acetate, and then excess dry HCl gas was purged for 1 h. The reaction solution was stirred for 2 h at room temperature, and the solvent was evaporated to dry under reduced pressure, to obtain the crude product. The crude product was rinsed with cyclohexane for 3 times and subjected to suction filtration. The filter cake was dried at 65° C. to obtain 87.6 mg of target compound 3 as a white solid, with a yield of 64%.

$^1$H NMR (400 MHz, DMSO-d$_6$): δ 10.78 (s, 1H), 7.23-7.31 (m, 3H), 5.32 (s, 2H), 4.42 (s, 2H), 2.94 (hept, J=6.9 Hz, 2H), 2.85 (s, 6H), 1.13 (d, J=6.8 Hz, 12H).

Boc-L-alanine (1.49 g, 7.87 mmol) and propofol chloroacetate (2 g, 7.85 mmol) were dissolved in DMF (10 mL) and stirred at room temperature for 40 min, to which was then added K$_2$CO$_3$ (1.19 g, 8.6 mmol). The reaction solution was stirred at 70° C. for 4 h and then filtered. The filtrate was extracted with ethyl acetate (100 mL) and water (50 mL). The organic layer was washed several times with water (3×50 mL) and dried over anhydrous sodium sulfate. The crude product was purified by column chromatography (cyclohexane/ethyl acetate, from 40:1 to 20:1) to give 2.18 g of intermediate a as a white solid, with a yield of 68%. Intermediate a (2.18 g, 5.35 mmol) was dissolved in 50 mL of ethyl acetate, and then dry HCl gas was purged for 1 h. Then, the reaction solution was stirred and reacted for 4 h at room temperature. Ethyl acetate was removed by evaporation under reduced pressure, to obtain a crude product. The crude product was rinsed with cyclohexane for 3 times, and then subjected to suction filtration. The filter cake was dried at 65° C. to obtain 1.28 g of target compound 4 as a white solid, with a yield of 69.6%.

$^1$H NMR (400 MHz, DMSO-d$_6$): δ 8.66 (s, 3H), 7.23-7.31 (m, 3H), 5.29 (d, J=2.4 Hz, 2H), 4.26 (q, J=7.1 Hz, 1H), 2.93 (hept, J=6.9 Hz, 2H), 1.48 (d, J=7.2 Hz, 3H), 1.13 (d, J=6.8 Hz, 12H).

Example 4

Example 5

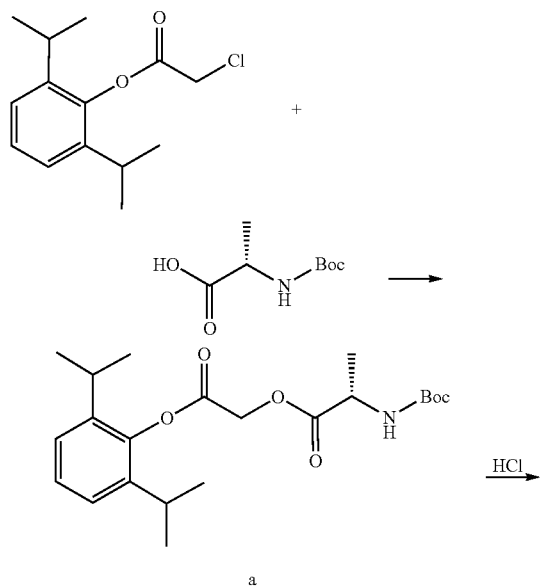

a

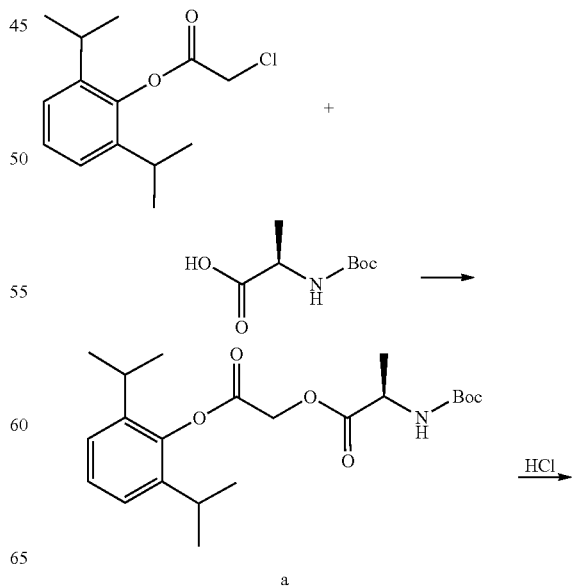

a

-continued

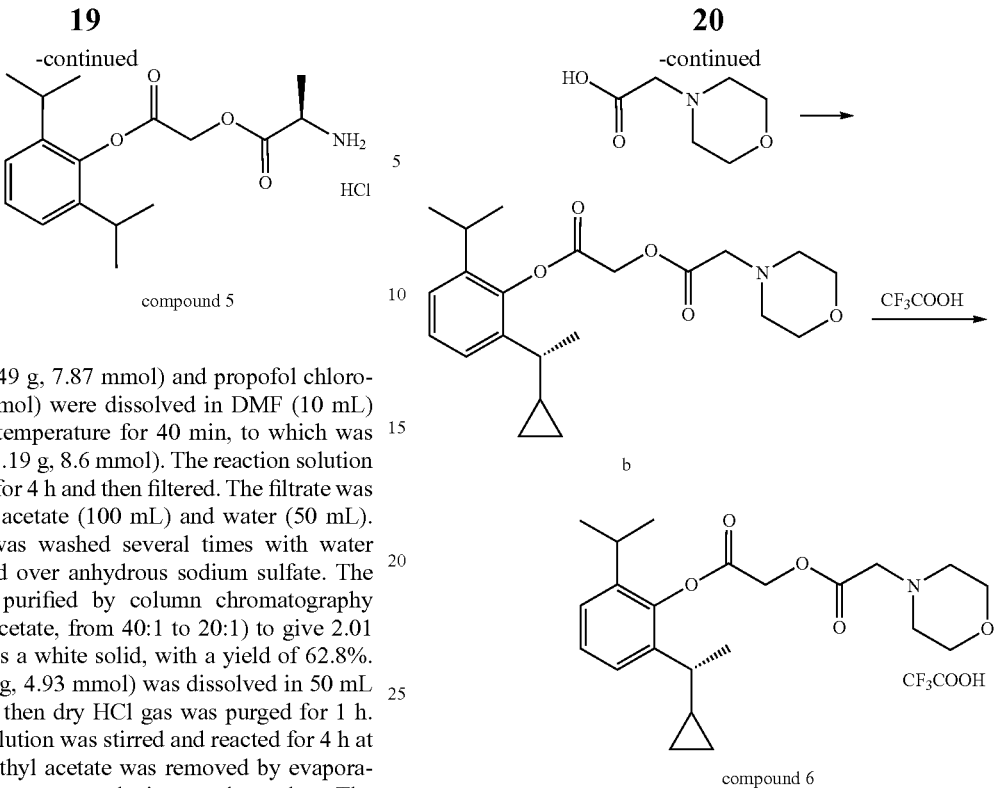

compound 5

Boc-D-alanine (1.49 g, 7.87 mmol) and propofol chloroacetate (2 g, 7.85 mmol) were dissolved in DMF (10 mL) and stirred at room temperature for 40 min, to which was then added K$_2$CO$_3$ (1.19 g, 8.6 mmol). The reaction solution was stirred at 70° C. for 4 h and then filtered. The filtrate was extracted with ethyl acetate (100 mL) and water (50 mL). The organic layer was washed several times with water (3×50 mL) and dried over anhydrous sodium sulfate. The crude product was purified by column chromatography (cyclohexane/ethyl acetate, from 40:1 to 20:1) to give 2.01 g of intermediate a as a white solid, with a yield of 62.8%. Intermediate a (2.01 g, 4.93 mmol) was dissolved in 50 mL of ethyl acetate, and then dry HCl gas was purged for 1 h. Then, the reaction solution was stirred and reacted for 4 h at room temperature. Ethyl acetate was removed by evaporation under reduced pressure, to obtain a crude product. The crude product was rinsed with cyclohexane for 3 times, and then subjected to suction filtration. The filter cake was dried at 65° C. to obtain 1.15 g of target compound 5 as a white solid, with a yield of 62.5%.

$^1$H NMR (400 MHz, DMSO-d$_6$): δ 8.69 (s, 3H), 7.21-7.30 (m, 3H), 5.24 (d, J=2.4 Hz, 2H), 4.29 (q, J=7.2 Hz, 1H), 2.91 (hept, J=6.9 Hz, 2H), 1.44 (d, J=7.2 Hz, 3H), 1.11 (d, J=6.8 Hz, 12H).

Example 6

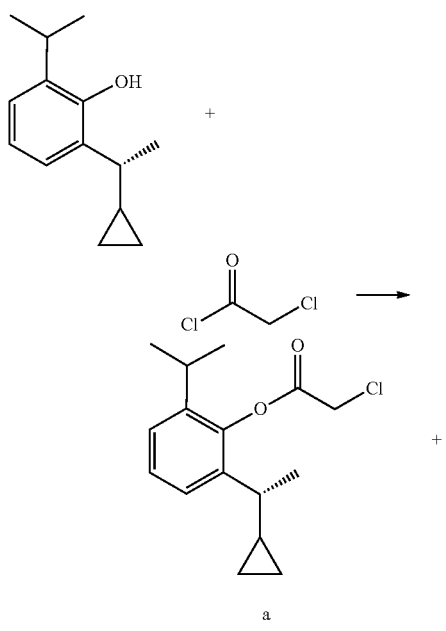

(R)-2-cyclopropylethyl-6-isopropylphenol (CAS: 1637741-58-2, 204 mg, 1 mmoL) and chloroacetyl chloride (124 mg, 1.1 mmoL) were dissolved in 10 mL of dichloromethane, to which was added pyridine (237 mg, 3 mmoL) in an ice bath, and then the reaction solution was warmed to room temperature and stirred for 2 h. The solvent was evaporated to dry. The residue was subjected to silica gel column chromatography (cyclohexane/ethyl acetate=20/1) to yield 186 mg of intermediate a as colorless oil, with a yield of 66%. Intermediate a (186 mg, 0.66 mmoL) and morpholin-4-ylacetic acid (96 mg, 0.66 mmoL) were dissolved in DMF (20 mL) and stirred for 40 min at room temperature, to which was then added K$_2$CO$_3$ (97 mg, 0.7 mmoL). The reaction solution was stirred at 70° C. for 4 h and cooled. Then, water (100 mL) was added, and the product was extracted with ethyl acetate (200 mL). The organic layer was washed with water (3×100 mL). The organic layer was separated and dried over anhydrous sodium sulfate. After filtration the next day, the filtrate was evaporated to remove the solvent and obtain the crude product, which was subjected to silica gel column chromatography (cyclohexane/ethyl acetate, 30:1), to provide 141 mg of intermediate b as colorless oil, with a yield of 55%. 141 mg of intermediate b was dissolved in 3 mL of trifluoroacetic acid, and stirred at room temperature for 30 min. The excess trifluoroacetic acid was removed by evaporation under reduced pressure, to which was added 20 mL of cyclohexane, and then the solid was precipitated. The solution was filtered, and the filter cake was dried at 65° C., to obtain 114.7 mg of white solid, with a yield of 63%.

$^1$H NMR (400 MHz, DMSO-d$_6$): δ 11.23 (s, 1H), 7.30-7.36 (3H, m), 5.36 (2H, s), 4.41 (2H, s), 3.82-3.89 (m, 4H), 3.21-3.28 (m, 5H), 2.55-2.58 (m, 1H), 1.31 (d, J=7.2 Hz, 3H), 1.26 (d, J=7.2 Hz, 6H), 1.03-1.07 (m, 1H), 0.42-0.52 (m, 2H), 0.17-0.25 (m, 2H).

Example 7

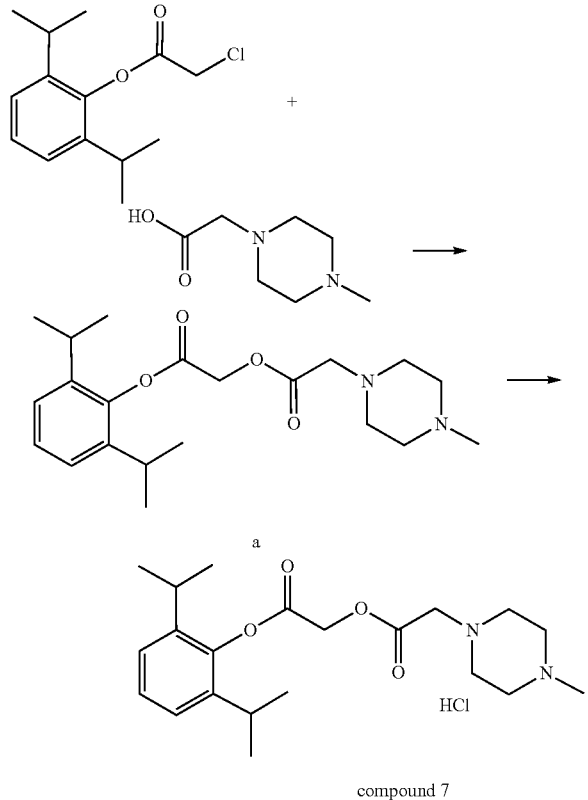

compound 7

Equimolar amounts of 4-methyl-1-piperazineacetic acid (CAS: 54699-92-2) and propofol chloroacetate were dissolved in DMF, to which was added two-fold excess of potassium carbonate, and then the reaction solution was stirred at 40° C. for 6 h. Following the work-up procedure in Example 3, intermediate a was prepared, and the yield was 46-68% based on the amount of propofol chloroacetate.

Intermediate a was dissolved in ethyl acetate, to which was purged dry HCl gas, and then the reaction solution was stirred at room temperature for 30 min. Ethyl acetate was removed by evaporation, and then the residue was dispersed in cyclohexane and subjected to suction filtration. The solid was rinsed for three times and filtered by suction. The filter cake was dried at 65° C. to obtain target compound 7 as a white solid, with a yield of 71-84%.

$^1$H NMR (400 MHz, DMSO-$d_6$): δ 11.07 (s, 1H), 7.20-7.27 (m, 3H), 5.19 (s, 2H), 3.85 (s, broad, 2H), 3.42-3.47 (m, 2H), 3.14-3.23 (m, 4H), 2.89-2.98 (m, 4H), 2.75 (s, 3H), 1.13 (d, J=6.9 Hz, 12H).

Example 8

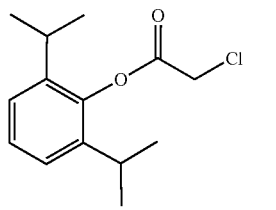

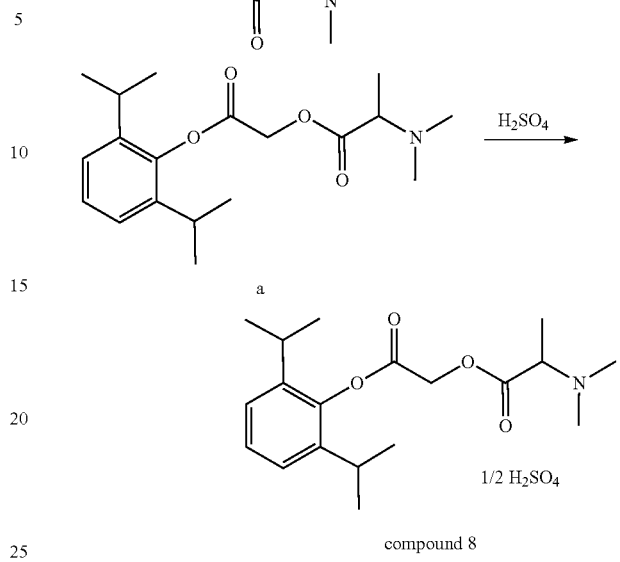

compound 8

Equimolar amounts of N,N-dimethylalanine (CAS: 19701-89-4) and propofol chloroacetate were dissolved in DMF, to which was added two-fold excess of potassium carbonate, and then the reaction solution was stirred at 40° C. for 6 h. Following the work-up procedure in Example 3, intermediate a was prepared, and the yield was 51-63% based on the amount of propofol chloroacetate.

Intermediate a was dissolved in ethanol, to which was added 0.5-fold molar amount of sulfuric acid, and then the reaction solution was stirred at room temperature for 30 min. Ethanol was removed by evaporation, and then the residue was dispersed in cyclohexane and subjected to suction filtration. The solid was rinsed for three times and filtered by suction. The filter cake was dried at 65° C. to obtain target compound 8 as a white solid, with a yield of 61-71%.

$^1$H NMR (400 MHz, DMSO-$d_6$): δ 8.91 (s, 1H), 7.25-7.33 (m, 3H), 5.21 (s, 2H), 4.27 (q, J=7.2 Hz, 1H), 2.95 (hept, J=6.8 Hz, 2H), 2.83 (s, 6H), 1.88 (d, J=7.2 Hz, 3H), 1.13 (d, J=6.8 Hz, 12H).

Example 9

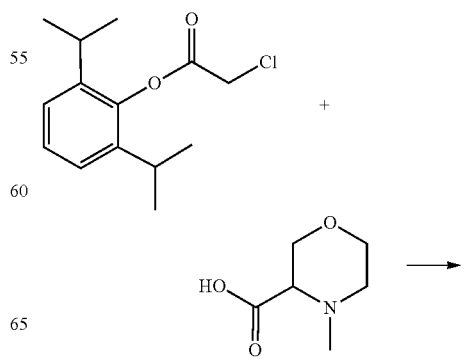

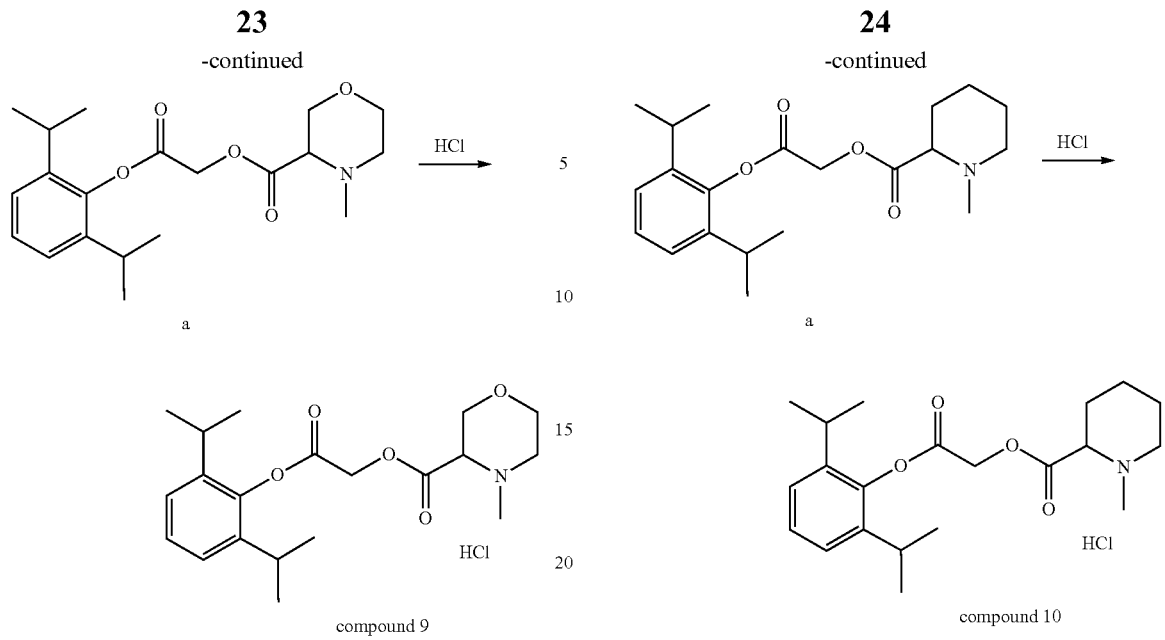

compound 9 compound 10

Equimolar amounts of 4-methyl-3-morpholinecarboxylic acid (CAS: 1240518-88-0) and propofol chloroacetate were dissolved in DMF, to which was added two-fold excess of potassium carbonate, and then the reaction solution was stirred at 40° C. for 6 h. Following the work-up procedure in Example 3, intermediate a was prepared, and the yield was 52-71% based on the amount of propofol chloroacetate.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed for three times and filtered by suction. The filter cake was dried at 65° C. to obtain target compound 9 as a white solid, with a yield of 49-71%.

$^1$H NMR (400 MHz, DMSO-d$_6$): δ 10.91 (s, 1H), 7.31-7.36 (m, 3H), 5.16 (s, 2H), 4.61-4.64 (m, 1H), 3.91-4.13 (m, 4H), 3.32-3.41 (m, 2H), 2.85 (s, 3H), 1.15 (d, J=6.8 Hz, 12H).

Equimolar amounts of 1-methylpiperidine-2-carboxylic acid (CAS: 7730-87-2) and propofol chloroacetate were dissolved in DMF, to which was added two-fold excess of potassium carbonate, and then the reaction solution was stirred at 40° C. for 6 h. Following the work-up procedure in Example 3, intermediate a was prepared, with a yield of 36-61%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed for three times and filtered by suction. The filter cake was dried at 65° C. to obtain target compound 10 as a white solid, with a yield of 45-68%.

$^1$H NMR (400 MHz, DMSO-d$_6$): δ 11.21 (s, 1H), 7.27-7.36 (m, 3H), 5.28 (s, 1H), 4.38-4.32 (m, 1H), 3.13-3.25 (m, 2H), 2.97 (hept, J=6.8 Hz, 2H), 2.91 (s, 3H), 2.01-2.18 (m, 2H), 1.71-1.75 (m, 2H), 1.13-1.35 (m, 14H).

Example 10

Example 11

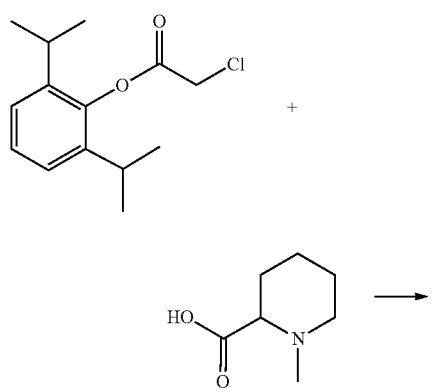

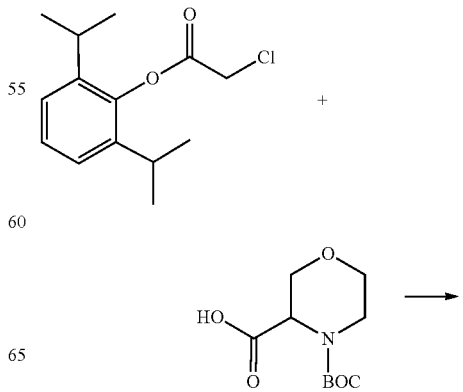

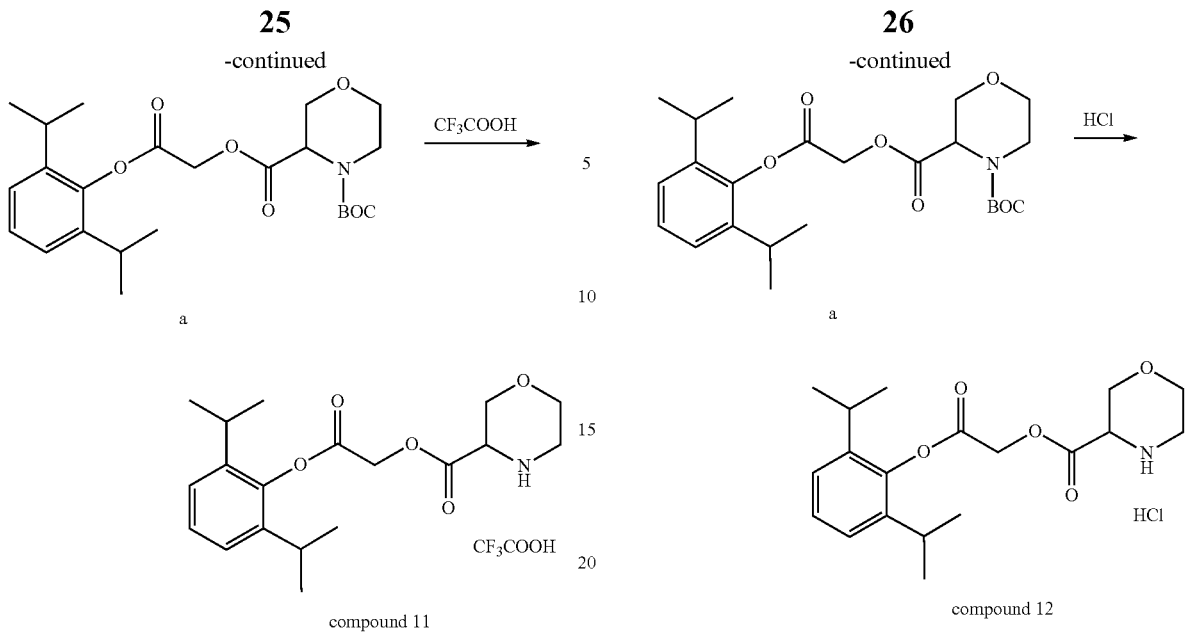

compound 11 compound 12

Equimolar amounts of 1-BOC-piperidin-2-carboxylic acid (CAS: 98303-20-9) and propofol chloroacetate were dissolved in DMF, to which was added two-fold excess of potassium carbonate, and then the reaction solution was stirred at 40° C. for 6 h. Following the work-up procedure in Example 5, intermediate a was prepared, with a yield of 56-71%.

Intermediate a was dissolved in excess trifluoroacetic acid, and then the reaction solution was stirred at room temperature for 6 h. Trifluoroacetic acid was removed by evaporation under reduced pressure, and then the residue was dispersed in cyclohexane and subjected to suction filtration. The solid was rinsed for three times and filtered by suction. The filter cake was dried at 65° C. to obtain target compound 11 as a white solid, with a yield of 55-63%.

$^1$H NMR (400 MHz, DMSO-d$_6$): δ 10.83 (s, 2H), 7.23-7.30 (m, 3H), 5.23 (s, 1H), 4.33-4.30 (m, 1H), 3.14-3.26 (m, 2H), 2.94 (hept, J=6.8 Hz, 2H), 2.03-2.16 (m, 2H), 1.72-1.77 (m, 2H), 1.12-1.34 (m, 14H).

Equimolar amounts of 4-BOC-morpholine-3-carboxylic acid (CAS: 212650-43-6) and propofol chloroacetate were dissolved in DMF, to which was added two-fold excess of potassium carbonate, and then the reaction solution was stirred at 40° C. for 6 h. Following the work-up procedure in Example 5, intermediate a was prepared, with a yield of 61-74%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed for three times and filtered by suction. The filter cake was dried at 65° C. to obtain target compound 12 as a white solid, with a yield of 55-78%.

$^1$H NMR (400 MHz, DMSO-d$_6$): δ 10.45 (s, 2H), 7.29-7.34 (m, 3H), 5.19 (s, 2H), 4.63-4.65 (m, 1H), 3.92-4.15 (m, 4H), 3.30-3.39 (m, 2H), 2.95 (hept, J=6.8 Hz, 2H), 1.13 (d, J=6.8 Hz, 12H).

Example 12

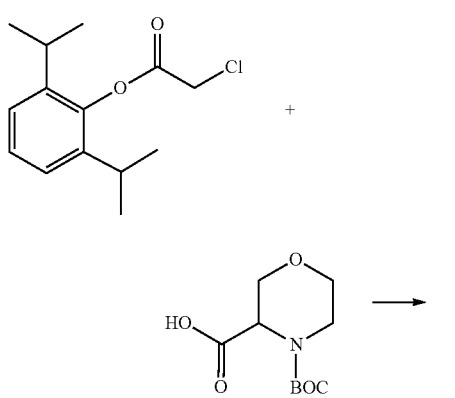

Example 13

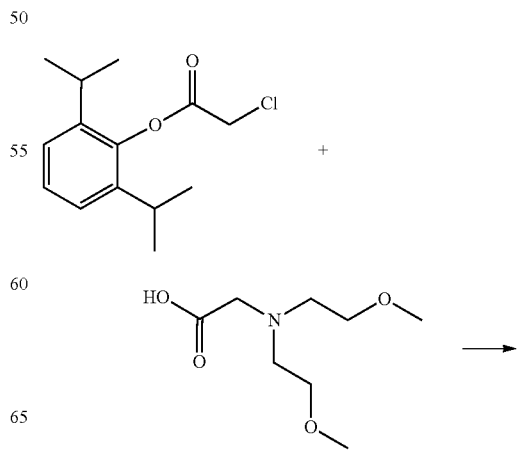

27

-continued

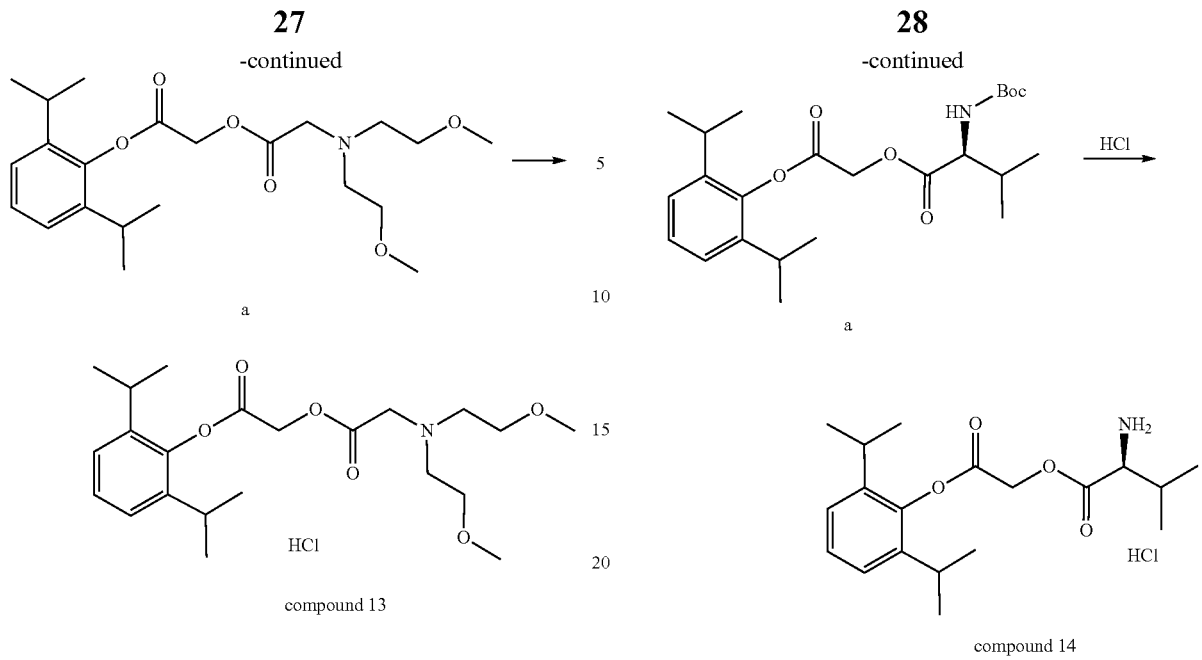

compound 13

Equimolar amounts of N,N-bis(2-methoxyethyl)ammonium acetate (CAS: 3235-71-0) and propofol chloroacetate were dissolved in DMF, to which was added two-fold excess of potassium carbonate, and then the reaction solution was stirred at 40° C. for 6 h. Following the work-up procedure in Example 3, intermediate a was prepared, with a yield of 41-61%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed with cyclohexane for three times and filtered by suction. The filter cake was dried at 65° C. to obtain target compound 13 as a white solid, with a yield of 65-69%.

$^1$H NMR (400 MHz, DMSO-$d_6$): δ 8.95 (s, 1H), 7.32-7.37 (m, 3H), 5.22 (s, 2H), 4.25 (s, 2H), 3.73-3.81 (m, 4H), 3.42-3.47 (m, 4H), 3.24 (s, 6H), 2.94 (hept, J=6.8 Hz, 2H), 1.13 (d, J=6.8 Hz, 12H).

Example 14

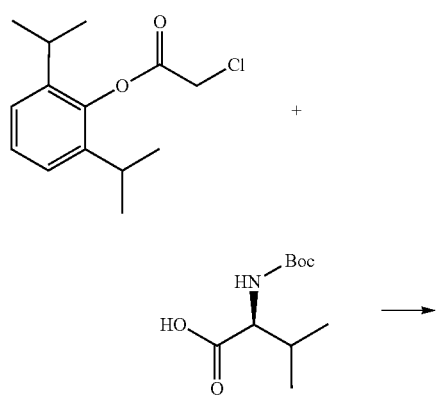

28

-continued compound 14

Equimolar amounts of BOC-L-valine (CAS: 13734-41-3) and propofol chloroacetate were dissolved in DMF, to which was added two-fold excess of potassium carbonate, and then the reaction solution was stirred at 40° C. for 6 h. Following the work-up procedure in Example 5, intermediate a was prepared, with a yield of 54-61%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed with cyclohexane for three times and filtered by suction. The filter cake was dried at 65° C. to obtain target compound 14 as a white solid, with a yield of 51-68%.

$^1$H NMR (400 MHz, DMSO-$d_6$): δ 8.91 (s, 3H), 7.31-7.35 (m, 3H), 5.22 (s, 2H), 4.16 (d, J=6.8 Hz, 1H), 2.96-3.04 (m, 3H), 1.13 (d, J=7.2 Hz, 12H), 0.96 (d, J=7.2 Hz, 6H).

Example 15

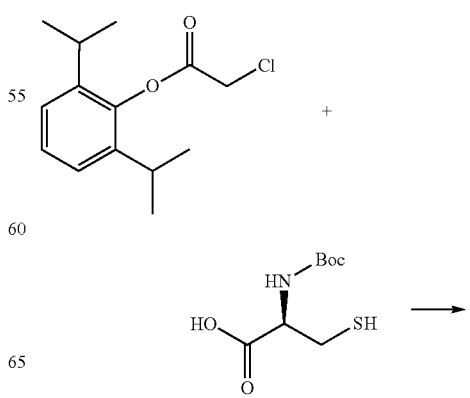

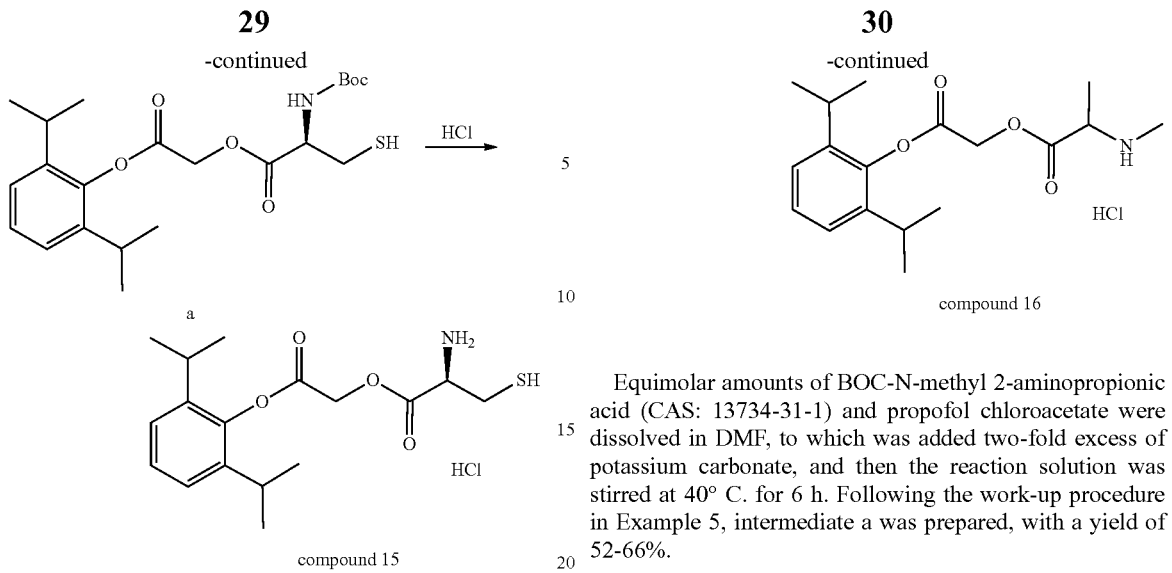

compound 15

Equimolar amounts of BOC-L-cysteine (CAS: 20887-95-0) and propofol chloroacetate were dissolved in DMF, to which was added two-fold excess of potassium carbonate, and then the reaction solution was stirred at 40° C. for 6 h. Following the work-up procedure in Example 5, intermediate a was prepared, with a yield of 49-72%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed with cyclohexane for three times and filtered by suction. The filter cake was dried at 65° C. to obtain target compound 15 as a white solid, with a yield of 67-73%.

$^1$H NMR (400 MHz, DMSO-d$_6$): δ 8.56 (s, 3H), 7.28-7.33 (m, 3H), 5.26 (s, 2H), 4.70 (t, J=6.8 Hz, 1H), 3.46-3.64 (m, 3H), 2.93 (hept, J=6.8 Hz, 2H), 1.16 (d, J=7.2 Hz, 6H).

Example 16

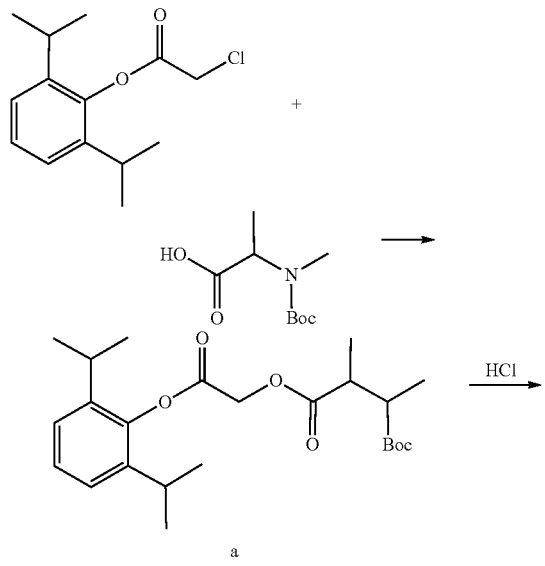

compound 16

Equimolar amounts of BOC-N-methyl 2-aminopropionic acid (CAS: 13734-31-1) and propofol chloroacetate were dissolved in DMF, to which was added two-fold excess of potassium carbonate, and then the reaction solution was stirred at 40° C. for 6 h. Following the work-up procedure in Example 5, intermediate a was prepared, with a yield of 52-66%.

Intermediate a was dissolved in ethyl acetate, to which was purged excess dry HCl gas, and then the reaction solution was stirred at room temperature for 30 min. Ethyl acetate was removed by evaporation, and then the residue was dispersed in cyclohexane and subjected to suction filtration. The solid was rinsed for three times and filtered by suction. The filter cake was dried at 65° C. to obtain target compound 16 as a white solid, with a yield of 61-69%.

$^1$H NMR (400 MHz, DMSO-d$_6$): δ 8.71 (s, 2H), 7.26-7.32 (m, 3H), 5.25 (s, 2H), 4.24 (q, J=7.2 Hz, 1H), 2.95 (hept, J=6.8 Hz, 2H), 2.84 (s, 3H), 1.88 (d, J=7.2 Hz, 3H), 1.13 (d, J=6.8 Hz, 12H).

Example 17

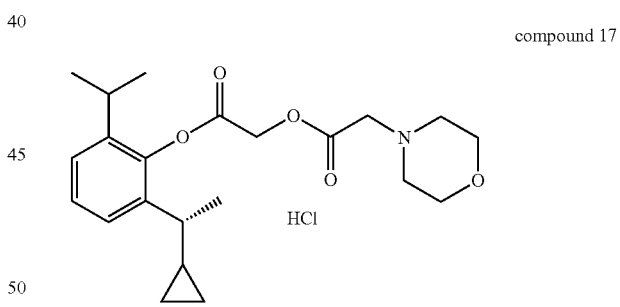

compound 17

Intermediate b mentioned in Example 6 was dissolved in ethyl acetate, to which was purged excess dry HCl gas, and then the reaction solution was stirred at room temperature for 30 min. The solvent was evaporated to dry under reduced pressure, and then the residue was dispersed in cyclohexane and subjected to suction filtration. The solid was rinsed with cyclohexane for three times and filtered by suction. The filter cake was dried at 65° C. to obtain target compound 17 as a white solid, with a yield of 51-64%.

$^1$H NMR (400 MHz, DMSO-d$_6$): δ 10.91 (s, 1H), 7.28-7.33 (3H, m), 5.29 (2H, s), 4.44 (2H, s), 3.78-3.85 (m, 4H), 3.22-3.27 (m, 5H), 2.55-2.59 (m, 1H), 1.34 (d, J=7.2 Hz, 3H), 1.24 (d, J=7.2 Hz, 6H), 1.01-1.06 (m, 1H), 0.41-0.51 (m, 2H), 0.18-0.24 (m, 2H).

Example 18

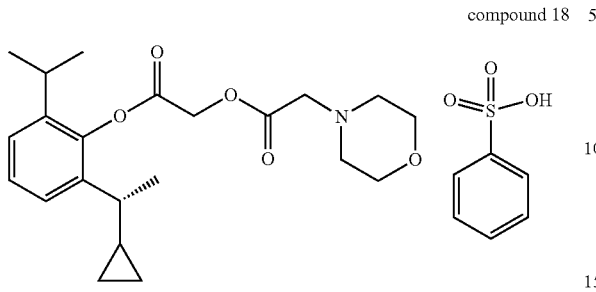

compound 18

Intermediate b mentioned in Example 6 was dissolved in absolute ethanol, to which was added equimolar benzenesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 18 as a white solid, with a yield of 70-84%.

$^1$H NMR (400 MHz, DMSO-$d_6$): δ 10.73 (s, 1H), 7.68-7.79 (m, 5H), 7.31-7.35 (3H, m), 5.29 (2H, s), 4.44 (2H, s), 3.81-3.89 (m, 4H), 3.22-3.26 (m, 5H), 2.57-2.59 (m, 1H), 1.32 (d, J=7.2 Hz, 3H), 1.28 (d, J=7.2 Hz, 6H), 1.04-1.07 (m, 1H), 0.41-0.52 (m, 2H), 0.16-0.23 (m, 2H).

Example 19

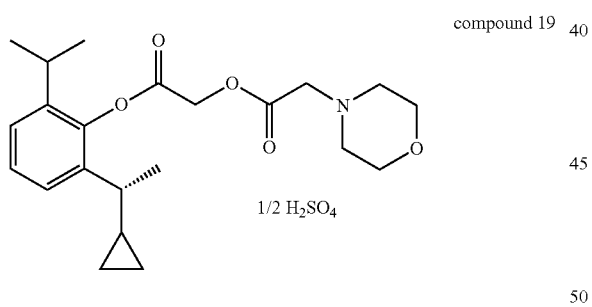

compound 19

1/2 H$_2$SO$_4$

Intermediate b mentioned in Example 6 was dissolved in absolute ethanol, to which was added 0.5 molar equivalents of sulfuric acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 19 as a white solid, with a yield of 80-88%.

$^1$H NMR (400 MHz, DMSO-$d_6$): δ 11.24 (s, 1H), 7.31-7.35 (3H, m), 5.33 (2H, s), 4.43 (2H, s), 3.83-3.89 (m, 4H), 3.19-3.26 (m, 5H), 2.53-2.57 (m, 1H), 1.29 (d, J=7.2 Hz, 3H), 1.25 (d, J=7.2 Hz, 6H), 1.02-1.07 (m, 1H), 0.39-0.51 (m, 2H), 0.18-0.26 (m, 2H).

Example 20

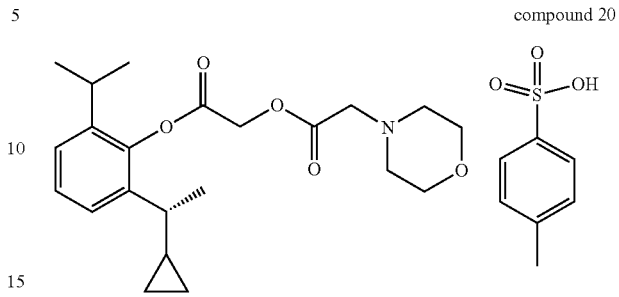

compound 20

Intermediate b mentioned in Example 6 was dissolved in absolute ethanol, to which was added equimolar p-toluenesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 20 as a white solid, with a yield of 75-86%.

$^1$H NMR (400 MHz, DMSO-$d_6$): δ 10.89 (s, 1H), 7.68-7.79 (m, 2H), 7.45-7.49 (m, 2H), 7.28-7.32 (3H, m), 5.24 (2H, s), 4.41 (2H, s), 3.80-3.87 (m, 4H), 3.19-3.23 (m, 5H), 2.53-2.55 (m, 1H), 2.43 (s, 3H), 1.33 (d, J=7.2 Hz, 3H), 1.25 (d, J=7.2 Hz, 6H), 1.02-1.05 (m, 1H), 0.40-0.51 (m, 2H), 0.17-0.23 (m, 2H).

Example 21 compound 21

Intermediate b mentioned in Example 6 was dissolved in absolute ethanol, to which was added equimolar methanesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 21 as a white solid, with a yield of 75-86%.

$^1$H NMR (400 MHz, DMSO-$d_6$): δ 11.21 (s, 1H), 7.28-7.32 (3H, m), 5.25 (2H, s), 4.43 (2H, s), 3.81-3.87 (m, 4H), 3.31 (s, 3H), 3.15-3.22 (m, 5H), 2.54-2.58 (m, 1H), 2.42 (s, 3H), 1.32 (d, J=7.2 Hz, 3H), 1.26 (d, J=7.2 Hz, 6H), 1.01-1.05 (m, 1H), 0.40-0.51 (m, 2H), 0.18-0.23 (m, 2H).

Example 22

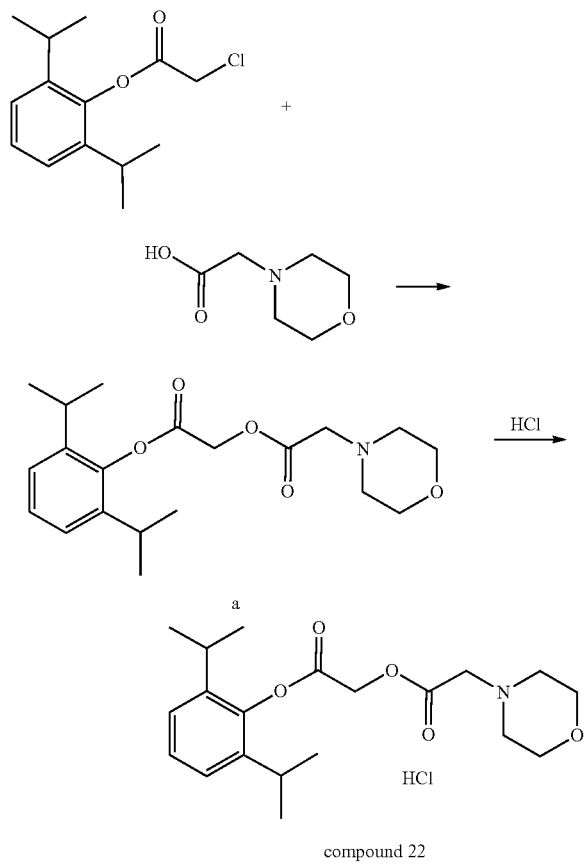

compound 22

Morpholin-4-ylacetic acid (2.29 g, 15.8 mmol), NaI (1.18 g, 15.8 mmol) and propofol chloroacetate (4 g, 15.8 mmol) were dissolved in DMF (20 ml), to which was added K$_2$CO$_3$ (2.25 g, 16.2 mmol), and then the reaction solution was stirred at 40° C. for 6 h. The reaction solution was cooled, and then extracted with ethyl acetate (200 mL) and water (100 mL). The organic layer was washed with water (3×100 mL) for several times. The organic layers were separated, dried over anhydrous sodium sulfate, and filtered the next day. The filtrate was evaporated to dryness under reduced pressure to obtain the crude product, which was purified by column chromatography (cyclohexane/ethyl acetate 30:1) to obtain 3.16 g of intermediate a as colorless oil, with a yield of 55.34%.

Intermediate a (1.02 g, 2.8 mmol) was dissolved in 30 mL of ethyl acetate, to which was purged dry HCl gas for 30 min, and then the reaction solution was stirred at room temperature for 1 h. Ethyl acetate was removed by evaporation under reduced pressure, to provide the crude product, which was rinsed with cyclohexane for many times and then subjected to suction filtration. Then, the filter cake was dried at 65° C. to obtain 0.78 g of target compound 22 as a white solid, with a yield of 70.91%.

$^1$H NMR (400 MHz, DMSO-d$_6$): δ 11.29 (s, 1H), 7.24-7.29 (m, 3H), 5.32 (s, 2H), 4.43 (s, 2H), 3.86 (s, broad, 4H), 3.25 (s, broad, 4H), 2.93 (hept, J=6.8 Hz, 2H), 1.13 (d, J=6.8 Hz, 12H).

Example 23

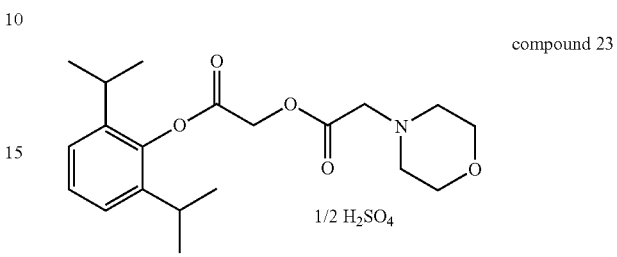

compound 23

Intermediate a mentioned in Example 22 was dissolved in absolute ethanol, to which was added 0.5 molar equivalents of sulfuric acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 23 as a white solid, with a yield of 70-85%.

$^1$H NMR (400 MHz, DMSO-d$_6$): δ 11.10 (s, 1H), 7.25-7.31 (m, 3H), 5.31 (s, 2H), 4.41 (s, 2H), 3.87 (s, broad, 4H), 3.26 (s, broad, 4H), 2.94 (hept, J=6.8 Hz, 2H), 1.14 (d, J=6.8 Hz, 12H).

Example 24

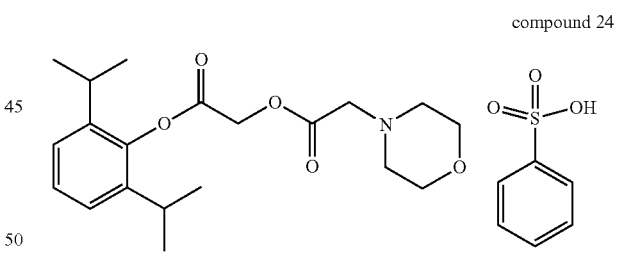

compound 24

Intermediate a mentioned in Example 22 was dissolved in absolute ethanol, to which was added equimolar benzenesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 24 as a white solid, with a yield of 71-79%.

$^1$H NMR (400 MHz, DMSO-d$_6$): δ 11.32 (s, 1H), 7.63-7.76 (m, 5H), 7.28-7.32 (m, 3H), 5.28 (s, 2H), 4.37 (s, 2H), 3.88 (s, broad, 4H), 3.28 (s, broad, 4H), 2.92 (hept, J=6.8 Hz, 2H), 1.13 (d, J=6.8 Hz, 12H).

Example 25

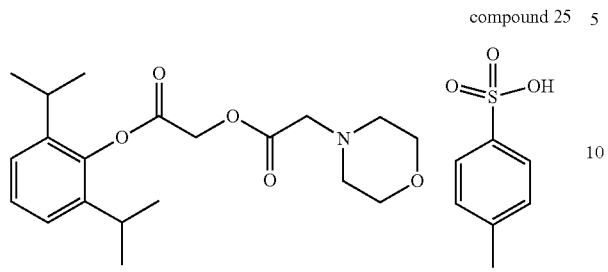

compound 25

Intermediate a mentioned in Example 22 was dissolved in absolute ethanol, to which was added equimolar p-toluenesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 25 as a white solid, with a yield of 75-89%.

$^1$H NMR (400 MHz, DMSO-d$_6$): δ 11.04 (s, 1H), 7.65-7.77 (m, 2H), 7.46-7.51 (m, 2H), 7.27-7.30 (m, 3H), 5.22 (s, 2H), 4.38 (s, 2H), 3.85 (s, broad, 4H), 3.23 (s, broad, 4H), 2.93 (hept, J=6.8 Hz, 2H), 1.15 (d, J=6.8 Hz, 12H).

Example 26

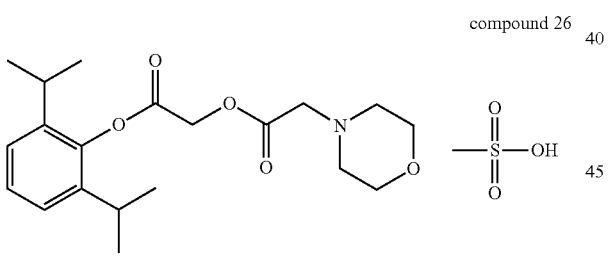

compound 26

Intermediate a mentioned in Example 22 was dissolved in absolute ethanol, to which was added equimolar methanesulfonic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 26 as a white solid, with a yield of 72-88%.

$^1$H NMR (400 MHz, DMSO-d$_6$): δ 11.16 (s, 1H), 7.29-7.31 (m, 3H), 5.22 (s, 2H), 4.37 (s, 2H), 3.84 (s, broad, 4H), 3.25-3.35 (m, 7H), 2.95 (hept, J=6.8 Hz, 2H), 1.13 (d, J=6.8 Hz, 12H).

Example 27

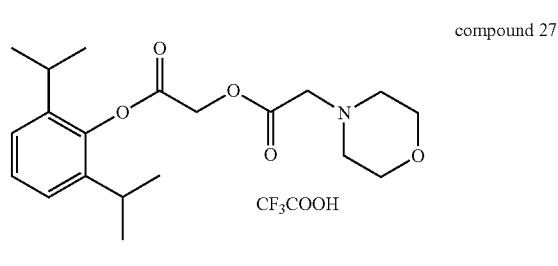 [SMILES: CC(C)c1cccc(C(C)C)c1OC(=O)COC(=O)CN1CCOCC1 ; "CF3COOH"]

compound 27

Intermediate a mentioned in Example 22 was dissolved in excess trifluoroacetic acid, and then the reaction solution was stirred at room temperature for 30 min. The solvent was evaporated to dry under reduced pressure, and then the residue was dispersed in cyclohexane and filtered. The solid was rinsed with cyclohexane for three times and subjected to suction filtration. The filter cake was dried at 65° C. to obtain target compound 27 as a white solid, with a yield of 68-79%.

$^1$H NMR (400 MHz, DMSO-d$_6$): δ 11.16 (s, 1H), 7.27-7.33 (m, 3H), 5.32 (s, 2H), 4.43 (s, 2H), 3.88 (s, broad, 4H), 3.25 (s, broad, 4H), 2.92 (hept, J=6.8 Hz, 2H), 1.13 (d, J=6.8 Hz, 12H).

Example 28

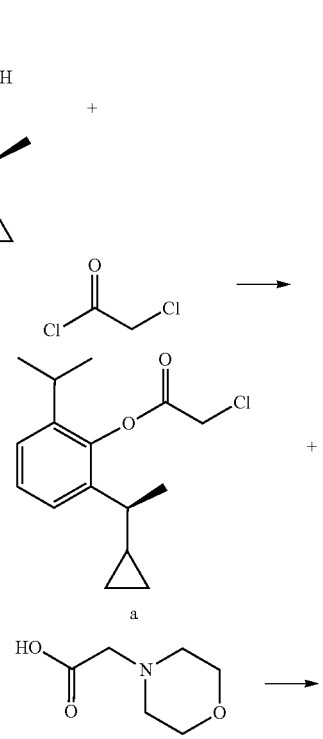

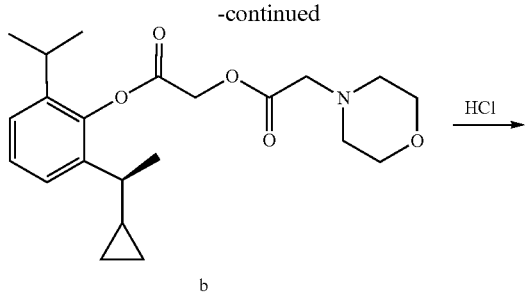

b

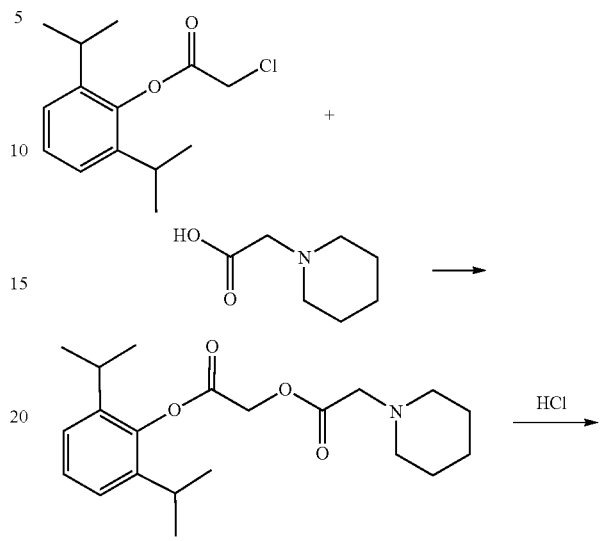

Example 29

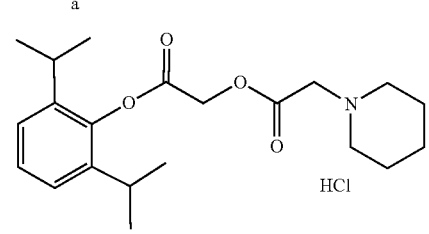

compound 28 compound 29

(R)-2-cyclopropylethyl-6-isopropylphenol (CAS: 1637-741-58-2, 204 mg, 1 mmol) and chloroacetyl chloride (124 mg, 1.1 mmol) were dissolved in 10 mL of dichloromethane, to which was added pyridine (237 mg, 3 mmol) in an ice bath, and then the reaction solution was warmed to room temperature and stirred for 2 h. The solvent was evaporated to dry. The residue was subjected to silica gel column chromatography (cyclohexane/ethyl acetate=20/1) to yield 176 mg of intermediate a as colorless oil. Intermediate a (176 mg, 0.62 mmol) and morpholin-4-ylacetic acid (90 mg, 0.66 mmol) were dissolved in DMF (20 mL) and stirred for 40 min at room temperature, to which was then added $K_2CO_3$ (97 mg, 0.7 mmol). The reaction solution was stirred at 70° C. for 4 h and cooled. Then, water (100 mL) was added, and the product was extracted with ethyl acetate (200 mL). The organic layer was washed with water (3×100 mL). The organic layer was separated and dried over anhydrous sodium sulfate. After filtration the next day, the filtrate was evaporated to remove the solvent and obtain the crude product, which was subjected to silica gel column chromatography (cyclohexane/ethyl acetate, 30:1), to provide 138 mg of intermediate b as colorless oil, with a yield of 54%. 138 mg of intermediate b was dissolved in 3 mL of ethyl acetate, to which was purged excess HCl gas, and then the reaction solution was stirred at room temperature for 30 min. The solvent was evaporated to dry under reduced pressure, and then 20 mL of cyclohexane was added to the residue. The solid was precipitated and collected by filtration, followed by rinsing with cyclohexane for 3 times and filtering. The filter cake was dried at 65° C., to obtain 101.2 mg of white solid, with a yield of 55.6%.

$^1$H NMR (400 MHz, DMSO-$d_6$): δ 11.61 (s, 1H), 7.31-7.38 (3H, m), 5.32 (2H, s) 4.39 (2H, s), 3.83-3.92 (m, 4H), 3.20-3.26 (m, 5H), 2.57-2.59 (m, 1H), 1.35 (d, J=7.2 Hz, 3H), 1.28 (d, J=7.2 Hz, 6H), 1.02-1.09 (m, 1H), 0.41-0.53 (m, 2H), 0.17-0.26 (m, 2H).

Piperidin-1-acetic acid (2.26 g, 15.8 mmol), NaI (1.18 g, 15.8 mmol) and propofol chloroacetate (4 g, 15.8 mmol) were dissolved in DMF (20 ml), to which was added $K_2CO_3$ (2.25 g, 16.2 mmol), and then the reaction solution was stirred at 40° C. for 6 h. The reaction solution was cooled, and then extracted with ethyl acetate (200 mL) and water (100 mL). The organic layer was washed with water (3×100 mL) for several times. The organic layers were separated, dried over anhydrous sodium sulfate, and filtered the next day. The filtrate was evaporated to dryness under reduced pressure to obtain the crude product, which was purified by column chromatography (cyclohexane/ethyl acetate 30:1) to obtain 3.31 g of intermediate a as colorless oil, with a yield of 58.1%.

Intermediate a (1.02 g, 2.8 mmol) was dissolved in 30 mL of ethyl acetate, to which was purged dry HCl gas for 30 min, and then the reaction solution was stirred at room temperature for 1 h. Ethyl acetate was removed by evaporation under reduced pressure, to provide the crude product, which was rinsed with cyclohexane for many times and then subjected to suction filtration. Then, the filter cake was dried at 65° C. to obtain 0.82 g of target compound 29 as a white solid, with a yield of 73.6%.

$^1$H NMR (400 MHz, DMSO-$d_6$): δ 10.53 (s, 1H), 7.2'-7.28 (m, 3H), 5.33 (s, 2H), 4.40 (s, 2H), 3.45-3.48 (m, 2H), 2.90-3.04 (m, 4H), 1.68-1.80 (m, 5H), 1.33-1.36 (m, 1H), 1.13 (d, J=6.9 Hz, 12H).

Example 30

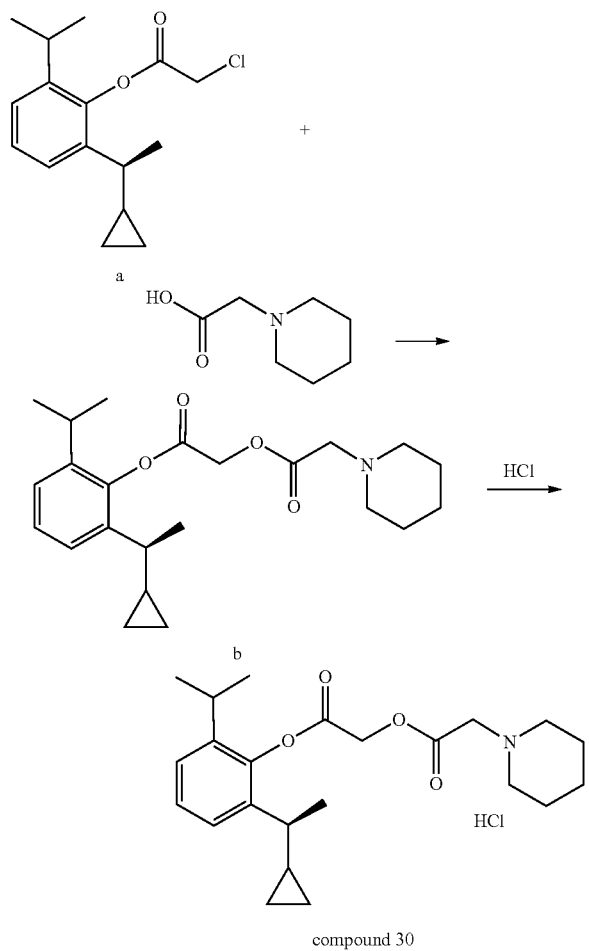

Intermediate a (176 mg, 0.62 mmoL) and piperidine-1-acetic acid (89 mg, 0.66 mmol) were dissolved in DMF (20 mL) and stirred at room temperature for 40 min, to which was then added $K_2CO_3$ (97 mg, 0.7 mmol). The reaction solution was stirred at 70° C. for 4 h, to which was added water (100 mL), and then extracted with ethyl acetate (200 mL). The organic layer was washed with water (3×100 mL), separated out, and dried over anhydrous sodium sulfate. The resultant solution was filtered the next day, and the filtrate was evaporated to remove the solvent and obtain the crude product, which was subjected to silica gel column chromatography (cyclohexane/ethyl acetate, 30:1), to provide 145 mg of intermediate b as colorless oil, with a yield of 60.4%.

145 mg of intermediate b was dissolved in 3 mL of ethyl acetate, to which was then purged excess HCl gas. Then, the reaction solution was stirred for 30 min at room temperature. The solvent was evaporated to dry under reduced pressure, and then 20 mL of cyclohexane was added to the residue. The solid was precipitated and collected by filtration, followed by rinsing with cyclohexane for 3 times and filtering. The filter cake was dried at 65° C., to obtain 110.2 mg of white solid, with a yield of 69.4%.

$^1$H NMR (400 MHz, DMSO-$d_6$): δ 11.12 (s, 1H), 7.29-7.37 (3H, m), 5.30 (2H, s) 4.35 (2H, s), 3.81-3.91 (m, 4H), 3.15-3.19 (m, 1H), 2.56-2.59 (m, 1H), 1.55-1.71 (m, 6H), 1.34 (d, J=7.2 Hz, 3H), 1.26 (d, J=7.2 Hz, 6H), 1.01-1.07 (m, 1H), 0.40-0.52 (m, 2H), 0.18-0.25 (m, 2H).

Example 31

According to the method described in Examples 1-30, the general preparation method of the target compound of formula (I) according to the present invention was as follows: equimolar amounts of substituted phenol chloroacetate and N-BOC-protected amino acids (the amino of amino acids whose amino hydrogen had been completely substituted did not need to be protected) were mixed in DMF, and then the reaction solution was stirred and reacted for 4-12 h at the temperature of r.t. to 70° C. (equimolar NaI could be added to promote the reaction). Then, the reaction solution was cooled, to which was added water to dissolve the inorganic salt, and then the solution was diluted with DMF. The resultant solution was extracted with ethyl acetate, and the organic layer was washed three times with water. The organic layers were separated, and dried over anhydrous sodium sulfate. The solution was filtered the next day. The filtrate was evaporated to remove the solvent and obtain a crude product, which was subjected to silica gel column chromatography, to obtain the free base of the target compound represented by formula (I), with a yield of 15%-80%. The free base and a suitable organic or inorganic acid are allowed to react in ethyl acetate or ethanol, to provide the corresponding salt. After the solvent was removed, the water-soluble salt of compound of formula (I) was obtained, with a yield of 35%-85%. The salts of the target compound of formula (I) that could be prepared by the above method (together with the main starting materials and the molecular ion peaks of products) included, but were not limited to:

TABLE 1

Structures and MS data of some compounds.

| Compound No. | Structure | Main starting materials | [M + H]$^+$ |
|---|---|---|---|
| Compound 31 | (structure shown) | (structures shown) | 350.4 |

TABLE 1-continued

Structures and MS data of some compounds.

| Compound No. | Structure | Main starting materials | [M + H]+ |
|---|---|---|---|
| Compound 32 | (2,6-diisopropylphenyl) ester structure with methionine · HCl | 2,6-diisopropylphenyl chloroacetate; Boc-Met-OH | 368.5 |
| Compound 33 | (2,6-diisopropylphenyl) ester structure with phenylalanine · HCl | 2,6-diisopropylphenyl chloroacetate; Boc-Phe-OH | 384.4 |
| Compound 34 | (2,6-diisopropylphenyl) ester structure with proline · HCl | 2,6-diisopropylphenyl chloroacetate; Boc-Pro-OH | 334.4 |
| Compound 35 | (2,6-diisopropylphenyl) ester structure with serine · HCl | 2,6-diisopropylphenyl chloroacetate; Boc-Ser-OH | 324.2 |
| Compound 36 | (2,6-diisopropylphenyl) ester structure with threonine · HCl | 2,6-diisopropylphenyl chloroacetate; Boc-Thr-OH | 324.3 |
| Compound 37 | (2,6-diisopropylphenyl) ester structure with azetidinyl acetate · HCl | 2,6-diisopropylphenyl chloroacetate; azetidinyl acetic acid | 334.4 |
| Compound 38 | (2,6-diisopropylphenyl) ester structure with N-methyl alanine · HCl | 2,6-diisopropylphenyl chloroacetate; N-Boc-N-methyl-alanine | 322.3 |

TABLE 1-continued

Structures and MS data of some compounds.

| Compound No. | Structure | Main starting materials | | [M + H]⁺ |
|---|---|---|---|---|
| Compound 39 | (2,6-diisopropylphenyl ester of glycolic acid esterified with N-methyl-L-alanine) · HCl | 2,6-diisopropylphenyl chloroacetate | N-Boc-N-methyl-L-alanine | 322.3 |
| Compound 40 | (2,6-diisopropylphenyl ester of glycolic acid esterified with N,N-dimethyl-L-alanine) · HCl | 2,6-diisopropylphenyl chloroacetate | N,N-dimethyl-L-alanine | 336.2 |
| Compound 41 | (2,6-diisopropylphenyl ester of glycolic acid esterified with N,N-dimethyl-D-alanine) · HCl | 2,6-diisopropylphenyl chloroacetate | N,N-dimethyl-D-alanine | 336.2 |
| Compound 42 | (2,6-diisopropylphenyl ester of glycolic acid esterified with pyrrolidinyl acetic acid) · HCl | 2,6-diisopropylphenyl chloroacetate | pyrrolidinyl acetic acid | 348.4 |
| Compound 43 | (2,6-diisopropylphenyl ester with hydroxy-N,N-dimethylglycine derivative) · 1/2 H₂SO₄ | 2,6-diisopropylphenyl chloroacetate | hydroxy-N,N-dimethylglycine | 338.3 |
| Compound 44 | (2,6-diisopropylphenyl ester with hydroxy-N-methylglycine derivative) · HCl | 2,6-diisopropylphenyl chloroacetate | N-Boc hydroxy-N-methylglycine | 334.3 |

TABLE 1-continued

Structures and MS data of some compounds.

| Compound No. | Structure | Main starting materials | [M + H]+ |
|---|---|---|---|
| Compound 45 | (2,6-diisopropylphenyl ester structure with SH) · HCl | (2,6-diisopropylphenyl chloroacetate); HO-CH2-C(O)-N(Boc)-CH2CH2-SH | 354.3 |
| Compound 46 | (2,6-diisopropylphenyl ester structure with N-Me, OMe) · HCl | (2,6-diisopropylphenyl chloroacetate); Cl-C(O)-CH2-N(Me)-CH2CH2-OMe | 366.2 |
| Compound 47 | (2,6-diisopropylphenyl ester structure with N(CH2CH2OH)2) · HCl | (2,6-diisopropylphenyl chloroacetate); HO-CH2-C(O)-N(CH2CH2OH)2 | 382.2 |
| Compound 48 | (2,6-diisopropylphenyl ester of leucine derivative) · HCl | (2,6-diisopropylphenyl chloroacetate); Boc-Leu-OH | 350.3 |
| Compound 49 | (2,6-diisopropylphenyl ester of proline derivative) · HCl | (2,6-diisopropylphenyl chloroacetate); Boc-Pro-OH | 334.2 |
| Compound 50 | (2,6-diisopropylphenyl ester of asparagine derivative) · HCl | (2,6-diisopropylphenyl chloroacetate); Boc-Asn-OH | 350.2 |
| Compound 51 | (2,6-diisopropylphenyl ester with morpholine) · HCl | (2,6-diisopropylphenyl chloroacetate); HO-CH2-C(O)-morpholine | 364.3 |

TABLE 1-continued

Structures and MS data of some compounds.

| Compound No. | Structure | Main starting materials | [M + H]⁺ |
|---|---|---|---|
| Compound 52 | (isopropyl/cyclopropyl-phenyl ester of morpholinoacetyloxyacetate) · citric acid | (2-isopropyl-6-(1-cyclopropylethyl)phenyl chloroacetate); morpholinoacetic acid | 390.2 |
| Compound 53 | (isopropyl/cyclopropyl-phenyl ester of piperidinoacetyloxyacetate) · HCl · citric acid | (2-isopropyl-6-(1-cyclopropylethyl)phenyl chloroacetate); piperidinoacetic acid | 388.2 |
| Compound 54 | (isopropyl/cyclopropyl-phenyl ester of pyrrolidinoacetyloxyacetate) · HCl | (2-isopropyl-6-(1-cyclopropylethyl)phenyl chloroacetate); pyrrolidinoacetic acid | 374.2 |
| Compound 55 | (isopropyl/cyclopropyl-phenyl ester of pyrrolidinoacetyloxyacetate, other enantiomer) · HCl | (2-isopropyl-6-(1-cyclopropylethyl)phenyl chloroacetate); pyrrolidinoacetic acid | 374.2 |

TABLE 1-continued

Structures and MS data of some compounds.

| Compound No. | Structure | Main starting materials | | [M + H]+ |
|---|---|---|---|---|
| Compound 56 | 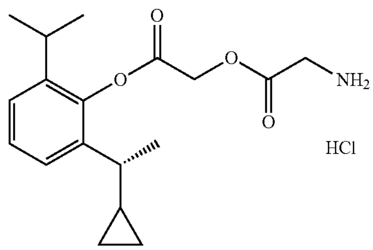 [SMILES: CC(C)c1cccc([C@H](C)C2CC2)c1OC(=O)COC(=O)CN ; Cl] | | | 320.4 |
| Compound 57 | 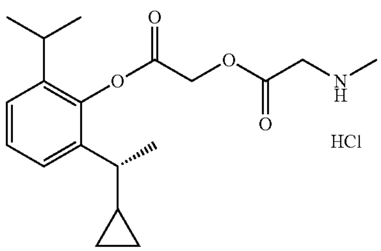 [SMILES: CNCC(=O)OCC(=O)Oc1c(C(C)C)cccc1[C@H](C)C1CC1 ; Cl] | | | 334.2 |
| Compound 58 | 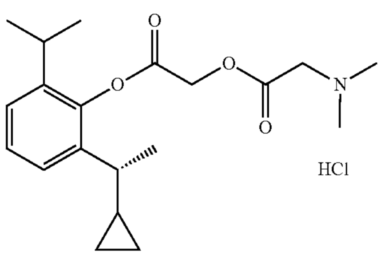 [SMILES: CC(C)c1cccc([C@H](C)C2CC2)c1OC(=O)COC(=O)CN(C)C ; Cl] | | | 348.3 |
| Compound 59 | 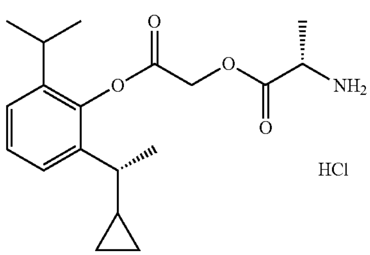 [SMILES: CC(C)c1cccc([C@H](C)C2CC2)c1OC(=O)COC(=O)[C@H](C)N ; Cl] | | | 334.2 |
| Compound 60 | 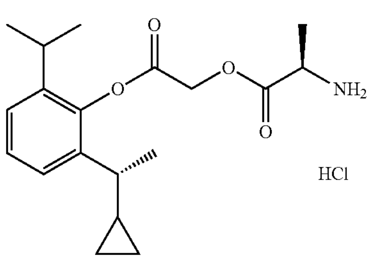 [SMILES: CC(C)c1cccc([C@H](C)C2CC2)c1OC(=O)COC(=O)[C@@H](C)N ; Cl] | | | 334.2 |

TABLE 1-continued

Structures and MS data of some compounds.

| Compound No. | Structure | Main starting materials | [M + H]+ |
|---|---|---|---|
| Compound 61 | (structure) HCl | (structures) | 388.3 |
| Compound 62 | (structure) HCl | (structures) | 320.4 |
| Compound 63 | (structure) HCl | (structures) | 334.2 |

Example 32

The prodrug to be tested was prepared into a saline solution of 10 mg/mL. 10 μL of drug-containing solution was added to 990 μL of mouse plasma, vortexed for 30 s, and then incubated at 37° C. At 30 s, 1 min, 5 min, 10 min, 30 min, 60 min and 120 min, 50 μL of drug-containing plasma was collected, to which was immediately added 150 μL of acetonitrile to terminate the enzymatic reaction, and then centrifuged at 20000 rpm and 4° C. for 10 min. 50 μL of supernatant was taken out and injected into HPLC, to determine the concentration of propofol by internal standard method. The decomposition rate of the prodrug was calculated from the concentrations of propofol or other substituted phenols. Chromatographic conditions: Agilent Zorbax XdB $C_{18}$ column (150 mm)×4.6 mm, 5 μm); column temperature 30° C.; the mobile phase, water:acetonitrile (40:60, v/v); fluorescence wavelength: excitation wavelength (Ex) at 276 nm, emission wavelength (EM) at 310 nm; flow rate: 1.2 mL/min; retention time: internal standard (thymol) 3.9 min, propofol 7.4 min. Linear range of propofol or other substituted phenols: 50-35000 ng/mL. Instruments: Waters 2695 high performance liquid chromatograph, Waters 2475 fluorescence detector. The experimental results for the breakdown of some prodrugs in plasma are shown in Table 2.

TABLE 2

The decomposition rates of prodrug molecules in plasma.

| Drugs | 30 s | 1 min | 5 min | 10 min | 30 min | 60 min | 120 min |
|---|---|---|---|---|---|---|---|
| fospropofol | — | — | — | — | 3% | 16% | 38% |
| Compound 1 | 97% | 100% | 100% | 100% | 100% | 100% | 100% |
| Compound 2 | 87% | 98% | 100% | 100% | 100% | 100% | 100% |
| Compound 3 | 51% | 67% | 80% | 90% | 97% | 100% | 100% |
| Compound 4 | 94% | 100% | 100% | 100% | 100% | 100% | 100% |
| Compound 7 | 91% | 100% | 100% | 100% | 100% | 100% | 100% |
| Compound 17 | 55% | 63% | 78% | 85% | 100% | 100% | 100% |
| Compound 22 | 58% | 66% | 80% | 89% | 100% | 100% | 100% |
| Compound 23 | 89% | 100% | 100% | 100% | 100% | 100% | 100% |
| Compound 27 | 60% | 65% | 79% | 86% | 100% | 100% | 100% |
| Compound 29 | 88% | 100% | 100% | 100% | 100% | 100% | 100% |
| Compound 37 | 75 | 92 | 100% | 100% | 100% | 100% | 100% |
| Compound 41 | 89 | 100% | 100% | 100% | 100% | 100% | 100% |
| Compound 42 | 91 | 100% | 100% | 100% | 100% | 100% | 100% |
| Compound 48 | 92 | 100% | 100% | 100% | 100% | 100% | 100% |

The in vitro decomposition experiment in plasma showed that the prodrug molecules of the present invention had a very fast decomposition rate in mouse plasma. After co-culturing with plasma for 30 s, 51%-98% of these prodrug molecules were decomposed in average, while the marketed drug fopropofol was still not decomposed significantly after co-culturing with plasma for 10 min, and only 38% was decomposed after co-culturing for 2 h, indicating that the decomposition rate of fospropofol in plasma was slow. The prodrug molecules prepared in the present invention could be rapidly decomposed in plasma to obtain propofol or other substituted phenols.

Example 33

For each drug, 10 male Kunming mice weighing 20-35 g were included, and the dose of each drug was 2×$ED_{50}$ in mice. After the compound of the present invention and fospropofol were respectively dissolved in saline, the resultant solutions were injected via the mouse tail vein. For propofol, a glucose dilution (5 mg/mL) of a commercially available emulsion of diprivan was selected and injected via the mouse tail vein; while, for another substituted phenol molecule (CAS:1637741-58-2), its 30% fat emulsion was prepared as a medicated emulsion. The concentration of the injectable solution of the compound according to the present invention was 10-15 mg/mL, and the concentration of the injectable solution of fospropofol was 55 mg/mL, while the concentration of the injectable solution of another substituted phenol molecule (CAS:1637741-58-2) was 1 mg/mL. After injection of tested drug, the occurrence time T1 of righting reflex after its disappearance, the duration T2 for the disappearance of righting reflex (i.e. anesthesia time) and the time T3 required for the animal to recover completely after waking up were recorded. Complete recovery refers to the recovery of autonomous activities of animals to the level before administration. In the experiment, animals were not given respiratory support such as oxygen inhalation or intubation.

TABLE 3

Anesthetic experiment of drugs.

| Drugs | Dose mg/kg | Propofol intake mg/kg | T1 min | T2 min | T3 min |
|---|---|---|---|---|---|
| Propofol | 25 | 25 | Immediate | 5-11.5 | 1-2 |
| Fospropofol | 168 | 90 | 1.5-2 | 28-45 | 5-8 |
| Compound 1 | 50 | 27 | Immediate | 6-12 | 1-2 |
| Compound 2 | 54 | 28 | Immediate | 7-15 | 1-2 |
| Compound 3 | 49 | 24.4 | Immediate | 5-10 | 1-2 |
| Compound 4 | 48 | 25 | Immediate | 5-13 | 1-2 |
| Compound 7 | 65.9 | 28.4 | Immediate | 6-13 | 1-2 |
| Compound 22 | 58 | 26 | Immediate | 4.5-10.5 | 1-2 |
| Compound 23 | 63.3 | 27.3 | Immediate | 5-13 | 1-2 |
| Compound 27 | 66 | 24.6 | Immediate | 4-12 | 1-2 |
| Compound 29 | 58.6 | 26.2 | Immediate | 5-14 | 1-2 |
| Compound 37 | 49.3 | 23.7 | Immediate | 4-10 | 1-2 |
| Compound 41 | 50.8 | 24.3 | Immediate | 5-13 | 1-2 |
| Compound 42 | 53.5 | 24.8 | Immediate | 6-12 | 1-2 |
| Compound 48 | 59.4 | 27.4 | Immediate | 6-14 | 1-2 |

T1: the onset time after injection;
T2: the duration of disappearance of righting reflex;
T3: the time required for righting reflex to recover to autonomous activity.

TABLE 4

Anesthetic experiment of other substituted phenols and their prodrug molecules.

| Drugs | Dose mg/kg | Intake of (R)-2-cyclo-propylethyl-6-isopropyl-phenol mg/kg | T1 min | T2 min | T3 min |
|---|---|---|---|---|---|
| (R)-2-cyclo-propylethyl-6-isopropyl-phenol | 3.2 | 3.2 | Immediate | 5-8 | 1-2 |
| Compound 17 | 6.7 | 3.2 | Immediate | 5.5-8 | 1-2 |
| Compound 19 | 7.9 | 3.3 | Immediate | 5.5-9 | 1-2 |
| Compound 53 | 7.1 | 3.4 | Immediate | 5-8.5 | 1-2 |
| Compound 55 | 7.0 | 3.5 | Immediate | 5-9 | 1-2 |

T1: the onset time after injection;
T2: the duration of disappearance of righting reflex;
T3: the time required for righting reflex to recover to autonomous activity.

The experimental results showed that the prodrug of the present invention had a very fast decomposition rate in plasma, and thus its onset time was equivalent to that of propofol. After injection, the animals can be anesthetized immediately. At the equivalent dose of the compound according to the present invention, the amount of propofol intaken by animals was equivalent to that intaken by animals anesthetized with propofol directly, while the amount of propofol carried by fospropofol was much higher than that intaken by animals anesthetized with propofol directly. Since the prodrugs according to the present invention carried significantly less propofol at effective doses than fospropofol, the duration of anesthesia for animals was significantly shorter than that of the marketed drug fospropofol; the time from awakening to complete recovery was also significantly shorter in the group of prodrugs according to the present invention than in fospropofol group. Similarly, the prodrug molecules of other substituted phenols according to the present invention also retained the characteristics of rapid onset and recovery of the prototype drug compared with the substituted phenol molecules carried by them.

In summary, the water-soluble prodrug molecules of the present invention had maintained the advantages of the substituted phenol anesthetic drugs including propofol, which had a fast onset of action and a fast recovery after withdrawal.

Example 34

Determination of therapeutic index (TI) of prodrug molecules: by referring the method in literature (Dixon, W. Staircase bioassay: the up-and-down method. Neurosci. Biobehav. Rev. 1991, 15, 47-50), the half-effective dose ($ED_{50}$) and half-lethal dose ($LD_{50}$) of the molecule to be tested were determined in Kunming mice (weighing 25-30 g, half male and half female). The therapeutic index for each molecule was calculated according to the equation: TI=$LD_{50}/ED_{50}$. Results are shown in Table 5.

TABLE 5

Therapeutic indexes of compounds.

| Compound No. | TI |
|---|---|
| Propofol | 4.4 |
| Fospropofol | 2.9 |
| Compound 7 | 3.9 |

TABLE 5-continued

Therapeutic indexes of compounds.

| Compound No. | TI |
| --- | --- |
| Compound 22 | 4.7 |
| Compound 23 | 4.4 |
| Compound 27 | 4.5 |
| Compound 29 | 4.1 |
| Compound 37 | 3.9 |
| Compound 41 | 3.8 |
| Compound 42 | 3.7 |
| Compound 48 | 4.1 |

The therapeutic index reflects the distance between the effective dose and the lethal dose of drugs, and was one of the most basic safety indicators of drug molecules. The experimental results showed that the therapeutic index of the compound according to the present invention was similar to that of propofol, and its safety was equivalent to that of propofol, which was significantly better than the marketed drug fospropofol. Because the therapeutic index of general anesthesia drugs was generally low (3-5), and for propofol, whose therapeutic window is not wide, its water-soluble prodrug can maintain a similar therapeutic index, indicating the high safety of these molecules.

The invention claimed is:

1. A compound of formula (I):

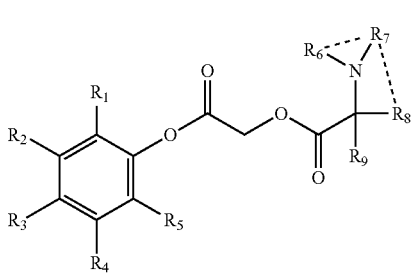

(I)

wherein:

$R_1$-$R_5$ are each independently selected from H, $C_{1-6}$ linear or branched or cyclic hydrocarbyl, halogen, $C_{1-4}$ alkoxy, cyano, nitro, ester group,

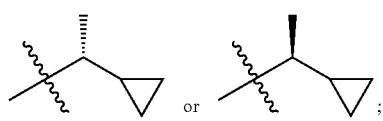

$R_6$-$R_9$ are each independently selected from H, and $C_{1-8}$ linear or branched or cyclic hydrocarbyl, or $R_6$ and $R_7$, or $R_7$ and $R_8$ are optionally covalently linked to form a cyclic hydrocarbyl;

H in the skeleton of $R_{1-9}$ are unsubstituted or substituted with a group selected from halogen, hydroxyl, sulfhydryl, carbamoyl, guanidyl, carboxyl, 4-imidazolyl, phenyl, hydroxyphenyl, and β-indolyl;

$R_{1-9}$ skeleton optionally contains one or more heteroatoms selected from O, S, and N; and with provisos that:

$R_6$ and $R_7$ are not simultaneously H, and when $R_7$ and $R_8$ are covalently linked, $R_7$ and $R_8$ are independently selected from $C_{1-3}$ alkylenes.

2. A salt of the compound of formula (I) according to claim 1 selected from acetate, adipate, alginate, 4-aminosalicylate, ascorbate, aspartate, glutamate, pyroglutamate, benzenesulfonate, benzoate, butyrate, camphorate, camphorsulfonate, carbonate, cinnamate, citrate, cyclohexaminesulfonate, cyclopentanepropionate, decanoate, 2,2-dichloroacetate, digluconate, dodecylsulphate, ethane-1,2-disulfonate, ethanesulfonate, formate, fumarate, mucate, gentisate, glucoheptanate, gluconate, glucuronate, glycerophosphate, hydroxyacetate, semisulfate, heptanoate, caproate, hippurate, hydrochloride, hydrobromide, hydroiodate, 2-hydroxyethanesulfonate, isobutyrate, lactate, lactobionate, laurate, malate, maleate, malonate, mandelate, methanesulfonate, naphthalene-1,5-disulfonate, 2-naphthalenesulfonate, nicotinate, nitrate, octanoate, oleate, orotate, oxalate, 2-oxoglutarate, palmitate, pamoate, pectinate, persulfate, 3-phenylpropionate, phosphate, picrate, pivalate, propionate, salicylate, sebacate, bisebacate, stearate, succinate, sulfate, tannate, tartrate, bitartrate, thiocyanate, toluenesulfonate or undecylate, hydrogen sulfate, sodium, and ammonium.

3. The compound of formula (I) according to claim 1, wherein: $R_1$-$R_5$ are each independently selected from H, and $C_{1-6}$ linear or branched or cyclic hydrocarbyl; and H in the skeleton of $R_{1-9}$ can be substituted with hydroxyl, sulfhydryl, carbamoyl, guanidyl, carboxyl, 4-imidazolyl, phenyl, hydroxyphenyl, and β-indolyl.

4. The compound of formula (I) according to claim 1, wherein: $R_1$-$R_5$ are each independently selected from H, and $C_{1-6}$ linear or branched or cyclic hydrocarbyl;

$R_6$ and $R_7$ are covalently linked, and $R_6$ and $R_7$ are independently selected from $C_{1-3}$ alkylenes; and $R_8$ and $R_9$ are each independently a $C_{1-8}$ linear or branched or cyclic hydrocarbyl.

5. The compound of formula (I) according to claim 1, wherein: $R_1$-$R_5$ are each independently selected from H, and $C_{1-6}$ linear or branched or cyclic hydrocarbyl;

$R_7$ and $R_8$ are covalently linked, and $R_7$ and $R_8$ are independently selected from $C_{1-3}$ alkylenes; and $R_6$ and $R_8$ are each independently selected from a $C_{1-8}$ linear or branched or cyclic hydrocarbyl.

6. The compound of formula (I) according to claim 1, wherein:

$R_1$ and $R_5$ are isopropyl;

$R_2$-$R_4$ are H;

$R_6$-$R_9$ are each independently selected from H, and $C_{1-8}$ linear or branched or cyclic hydrocarbyl;

H in the skeleton of $R_{1-9}$ are unsubstituted or substituted with a group selected from halogen, hydroxyl, sulfhydryl, carbamoyl, guanidyl, carboxyl, 4-imidazolyl, phenyl, hydroxyphenyl, and β-indolyl;

$R_{1-9}$ skeleton optionally contains one or more heteroatoms selected from O, S, and N, with provisos that:

$R_6$ and $R_7$ are not simultaneously H;

when $R_6$ and $R_7$ are covalently linked, $R_6$ and $R_7$ are independent selected from $C_{1-3}$ alkylenes; and when $R_7$ and $R_8$ are covalently linked, $R_7$ and $R_8$ are selected from $C_{1-3}$ alkylenes.

7. The compound of formula (I) according to claim 1, wherein:

$R_1$ is isopropyl;

$R_5$ is

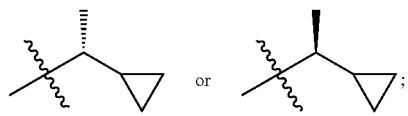 or ;

$R_2$-$R_4$ are H;

$R_6$-$R_9$ are each independently selected from the group consisting of H, and $C_{1-8}$ linear or branched or cyclic hydrocarbyl;

H in the skeleton of $R_{1-9}$ is unsubstituted or substituted with a group selected from halogen, hydroxyl, sulfhydryl, carbamoyl, guanidyl, carboxyl, 4-imidazolyl, phenyl, hydroxyphenyl, and β-indolyl;

$R_{1-9}$ skeleton optionally contain heteroatoms selected from O, S, and N, with provisos that:

$R_6$ and $R_7$ are not simultaneously H;

when $R_6$ and $R_7$ are covalently linked, $R_6$ and $R_7$ are independently selected from $C_{1-3}$ alkylenes; and when $R_7$ and $R_8$ are covalently linked, $R_7$ and $R_8$ are independently selected from $C_{1-3}$ alkylenes.

8. The compound of formula (I) according to claim 1 selected from:

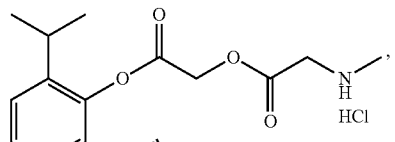

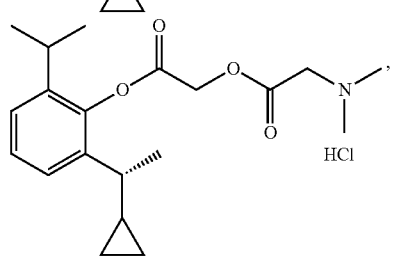

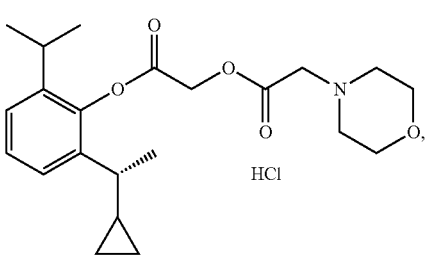

-continued

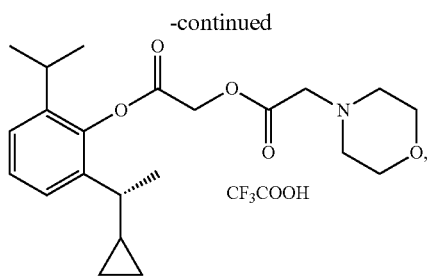

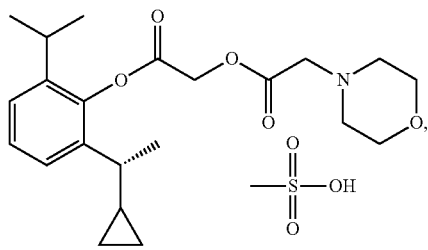

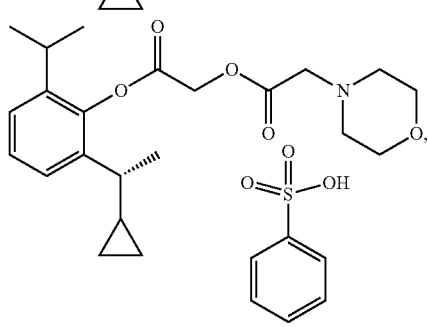

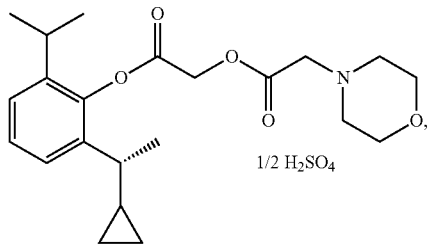

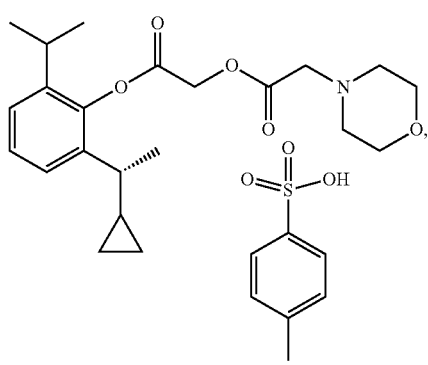

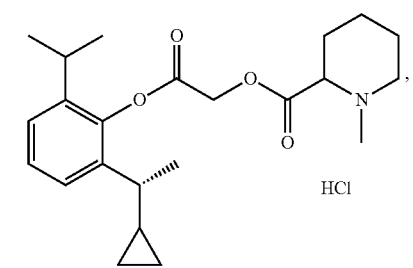

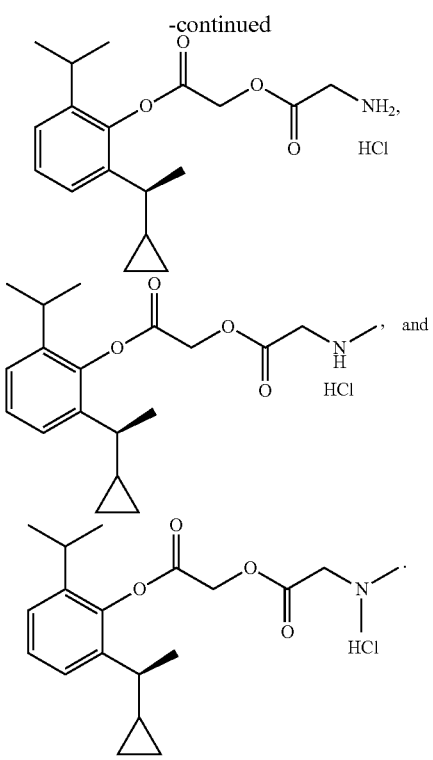
9. The compound of formula (I) according to claim 1 selected from:
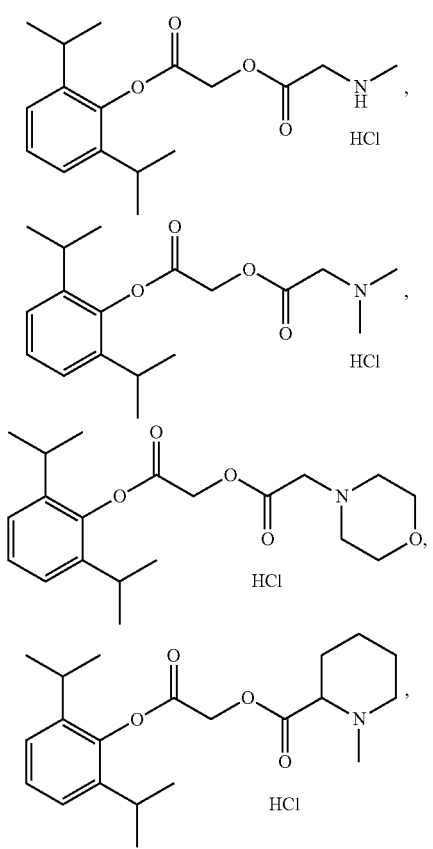
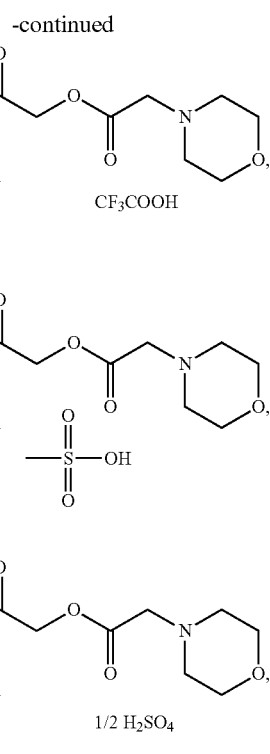
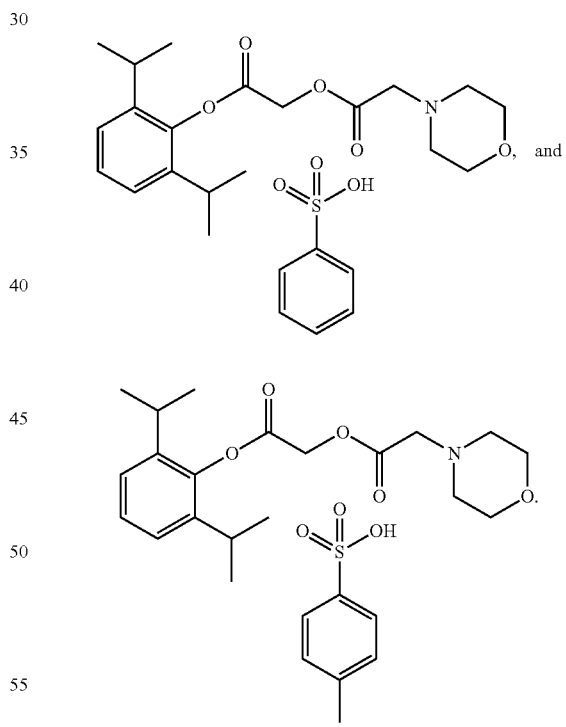
10. A pharmaceutical composition comprising the compound of formula (I) according to claim 1, or a stereoisomer, an isotopically substituted compound, a pharmaceutically acceptable salt, or a solvate thereof, and pharmaceutically acceptable excipients, carriers, or adjuvents.
* * * * *